(12) United States Patent
Arafune

(10) Patent No.: US 8,942,822 B2
(45) Date of Patent: Jan. 27, 2015

(54) VISUAL APPARATUS AND VISUAL METHOD

(71) Applicant: Sony Corporation, Tokyo (JP)

(72) Inventor: Akira Arafune, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/061,788

(22) Filed: Oct. 24, 2013

(65) Prior Publication Data
US 2014/0121738 A1 May 1, 2014

(30) Foreign Application Priority Data

Oct. 31, 2012 (JP) .................. 2012-241292

(51) Int. Cl.
*A61N 1/00* (2006.01)
*A61N 1/05* (2006.01)
(52) U.S. Cl.
CPC .................. *A61N 1/0543* (2013.01)
USPC .......................................... 607/116

(58) Field of Classification Search
CPC ....... A61N 1/05; A61N 1/056; A61N 1/0543; A61N 1/36046
USPC .......................................... 607/116
See application file for complete search history.

(56) References Cited

U.S. PATENT DOCUMENTS 7,079,900 B2 * 7/2006 Greenburg et al. ............. 607/54

FOREIGN PATENT DOCUMENTS

JP 2009-254489 11/2009

* cited by examiner

*Primary Examiner* — George Manuel
(74) *Attorney, Agent, or Firm* — Rader, Fishman & Grauer PLLC

(57) ABSTRACT

A visual apparatus includes at least one set of probes and a signal generation unit. The at least one set of probes includes a plurality of probes. The signal generation unit is configured to generate a stimulation pattern signal corresponding to information on color, and to input, to at least a part of an area ranging from a retina to a visual nerve, a plurality of pattern signals as the generated stimulation pattern signal via the plurality of probes in the at least one set of probes.

15 Claims, 29 Drawing Sheets

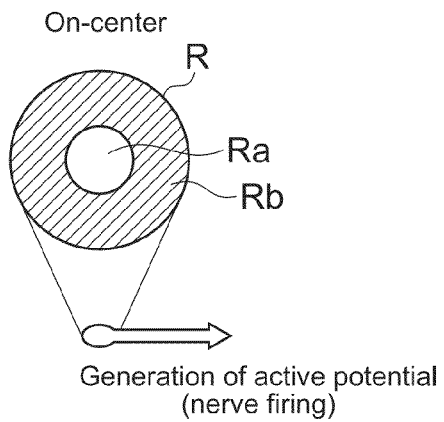
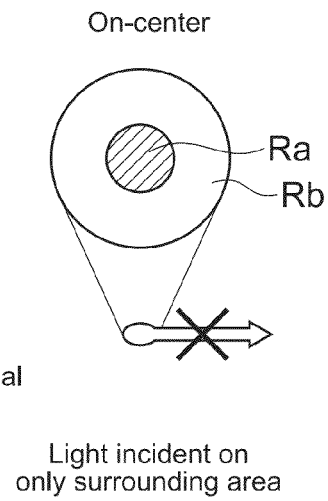
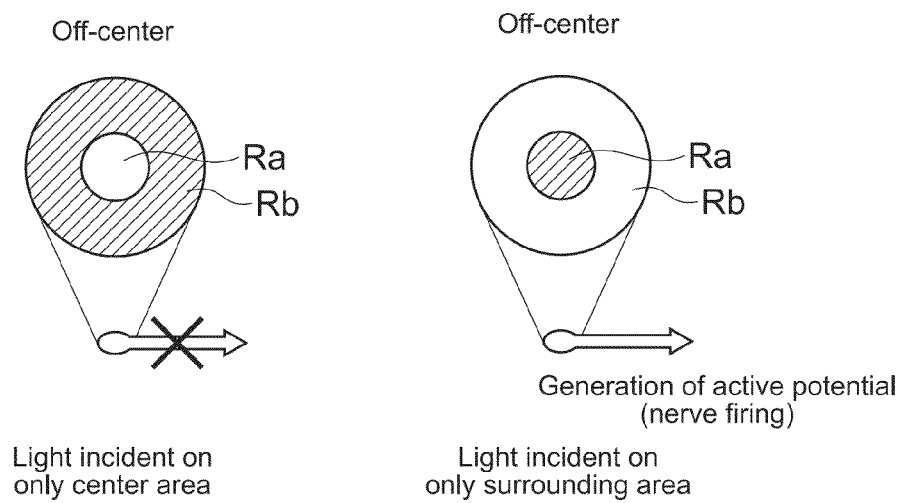
FIG.2A — On-center, Light incident on only center area, Generation of active potential (nerve firing)
FIG.2B — On-center, Light incident on only surrounding area
FIG.2C — Off-center, Light incident on only center area
FIG.2D — Off-center, Light incident on only surrounding area, Generation of active potential (nerve firing)

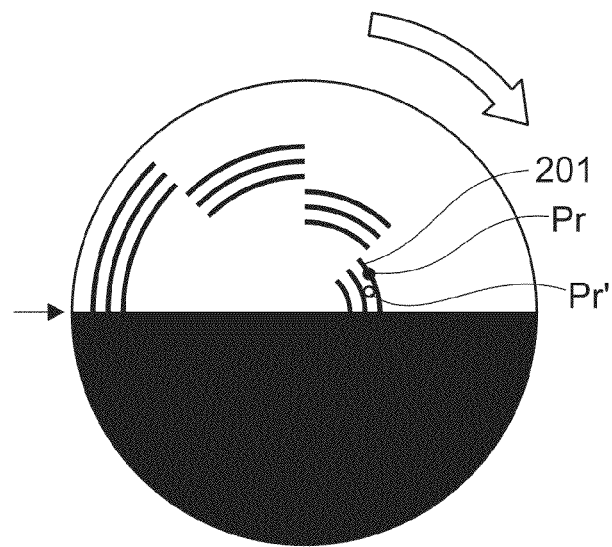
FIG.6A
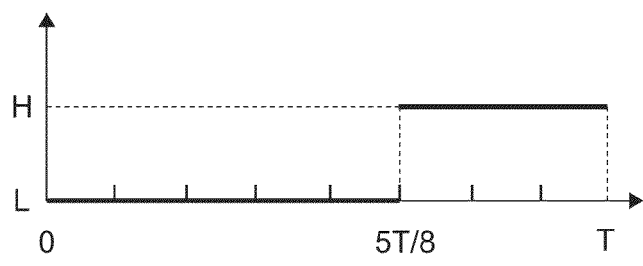
Point Pr
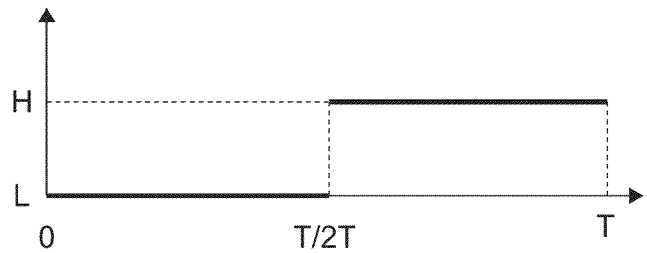
Point Pr'
Stimulation pattern P1 (red)
FIG.6B

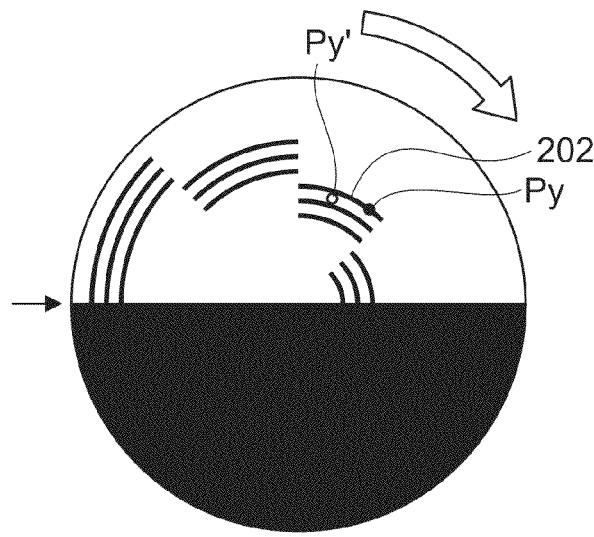
FIG.7A
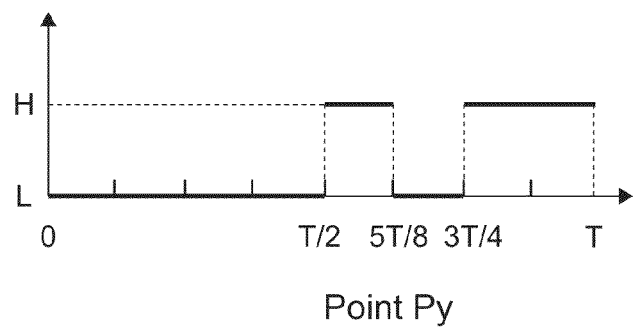
Point Py
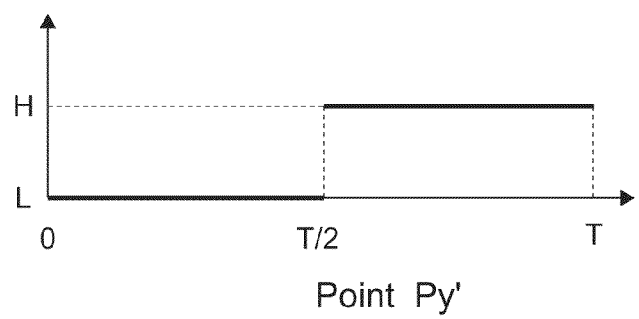
Point Py'
Stimulation pattern P2 (yellow)
FIG.7B

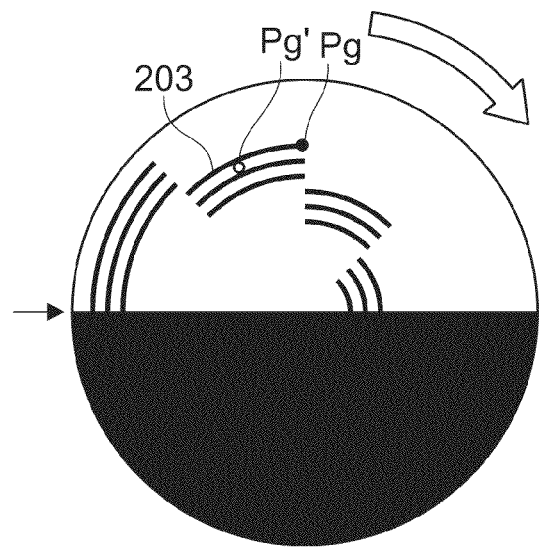
FIG.8A
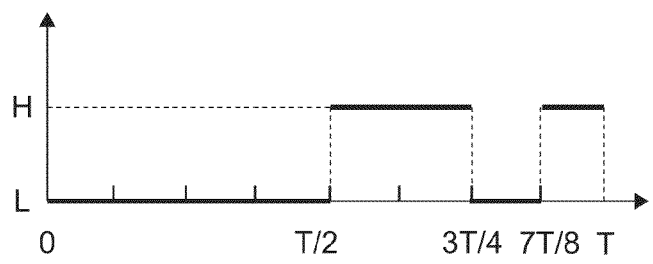
Point Pg
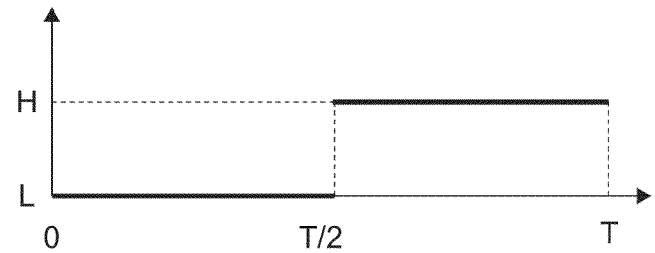
Point Pg'
Stimulation pattern P3 (green)
FIG.8B

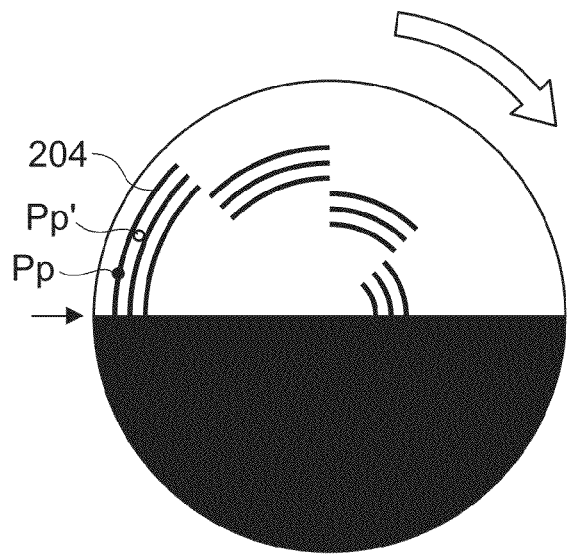
FIG.9A
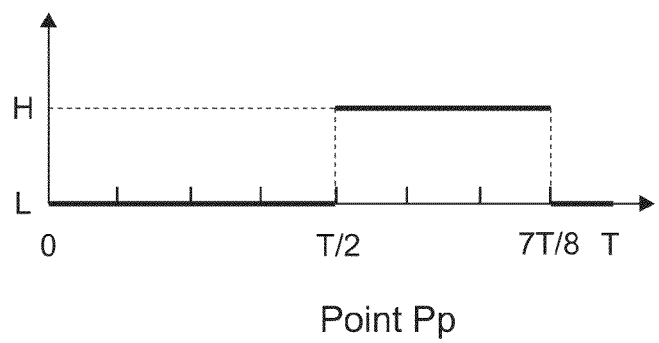
Point Pp
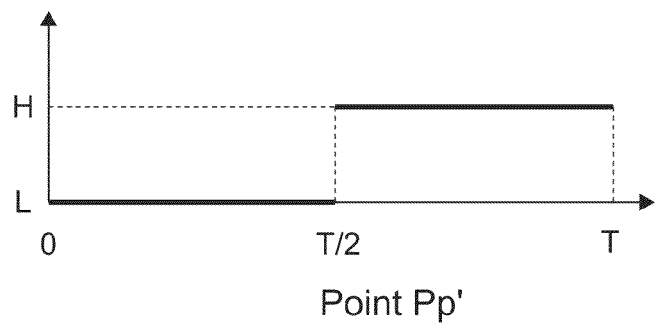
Point Pp'
Stimulation pattern P4 (purple)
FIG.9B Example 5
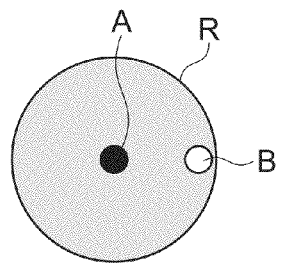
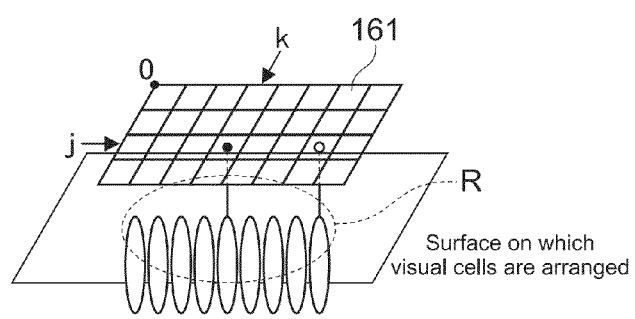
Example 6
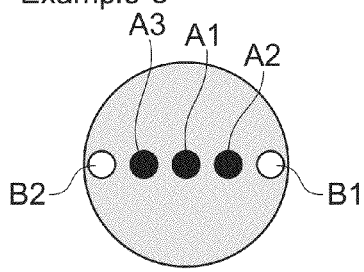
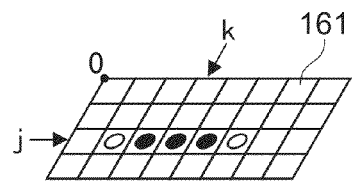
Example 7
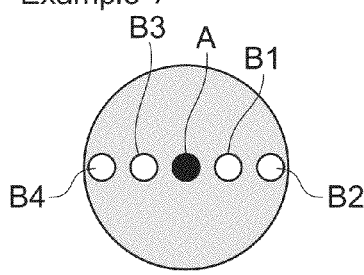
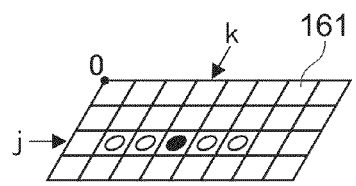
FIG.13

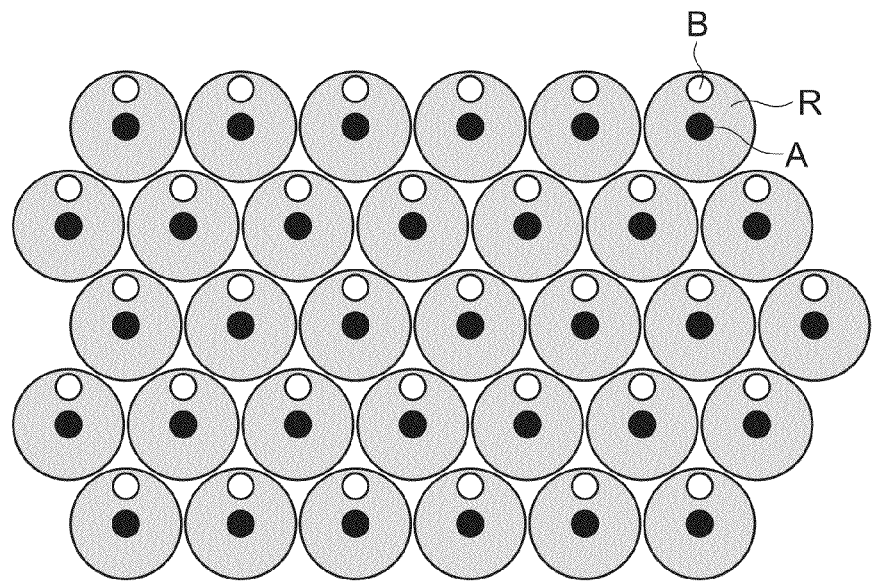
FIG.17A
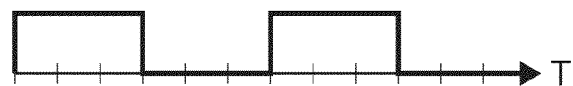
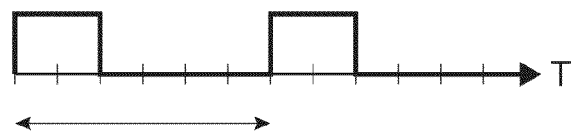
T = 0.14sec
tick = 0.024sec
FIG.17B

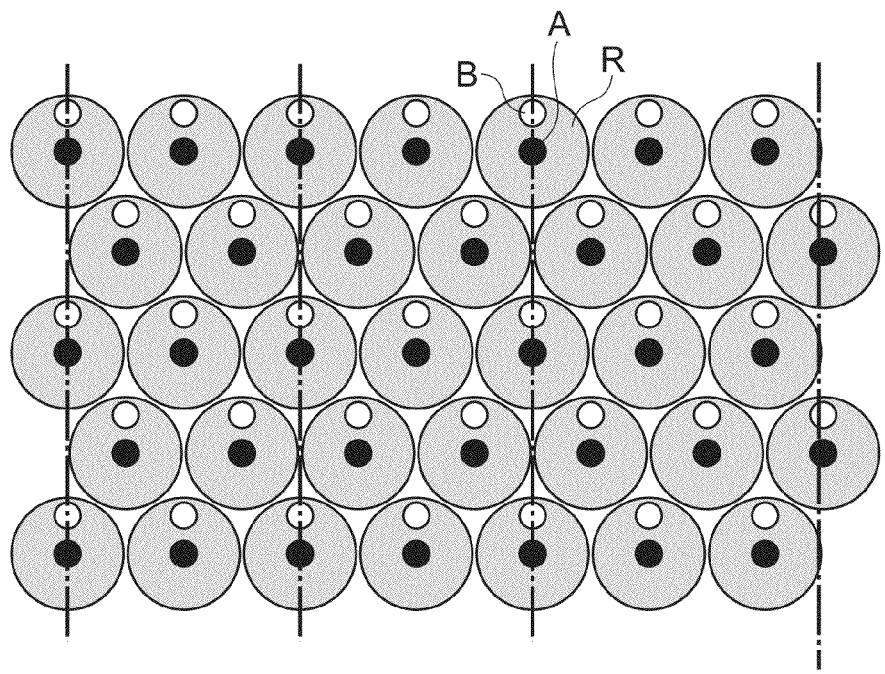
FIG.18A
Electrode A arranged on line
→ T
Electrode B arranged on line
→ T
Sets of electrodes other than those arranged on line
———————— (no change)
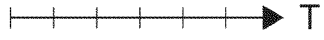
→ T
FIG.18B

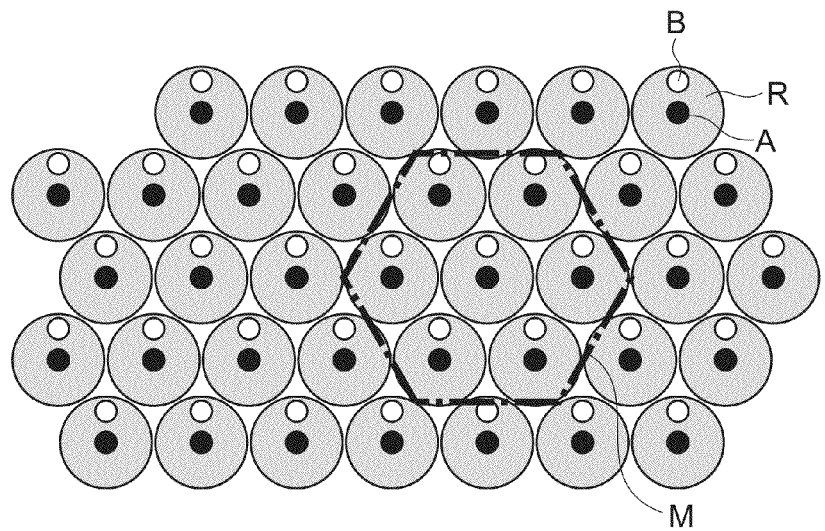

FIG.19A

Electrode A in alternate long
and short dash line

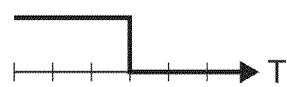

Electrode B in alternate long
and short dash line

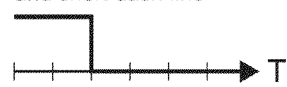

Sets of electrodes outside
alternate long and short dash line
─────────────── (no change)

FIG.19B

Electrode A outside alternate long
and short dash line

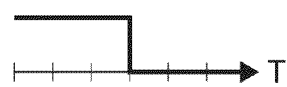

Electrode B outside alternate long
and short dash line

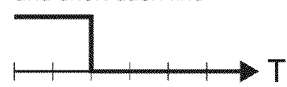

Sets of electrodes in alternate long
and short dash line
─────────────── (no change)

FIG.19C

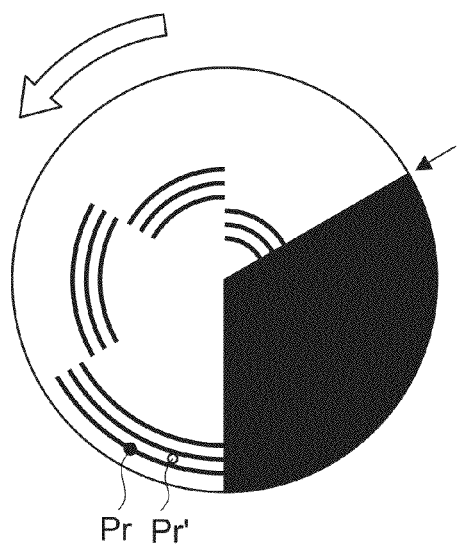
FIG.24A
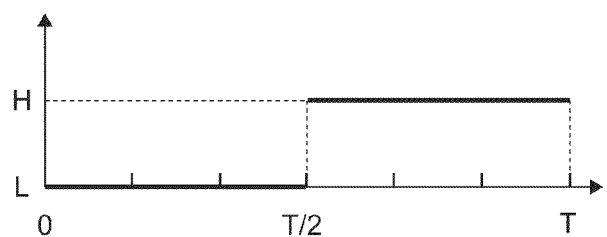
Point Pr
Point Pr'
Stimulation pattern P5 (red)
FIG.24B

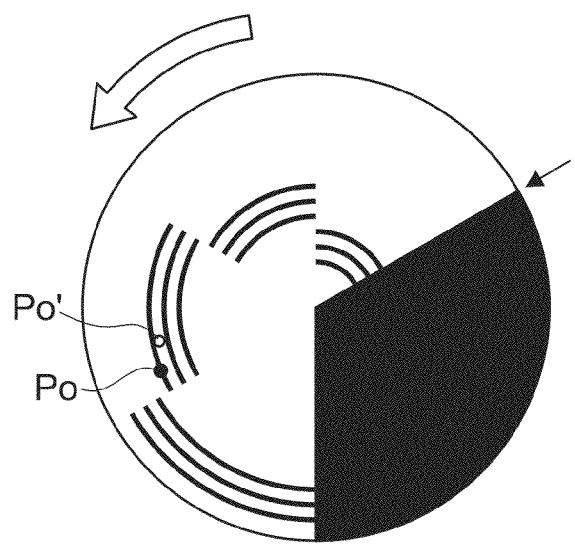
FIG.25A
Point Po
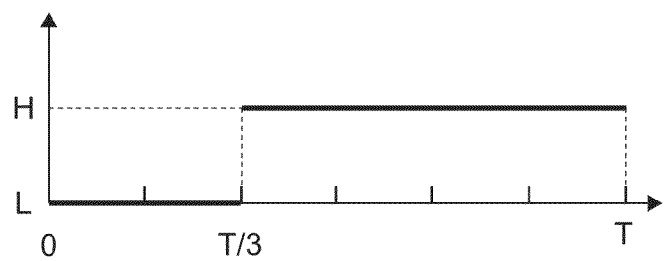
Point Po'
Stimulation pattern P6 (orange)
FIG.25B

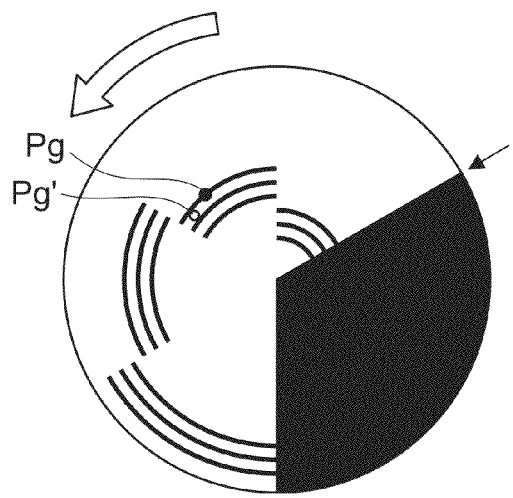
FIG.26A
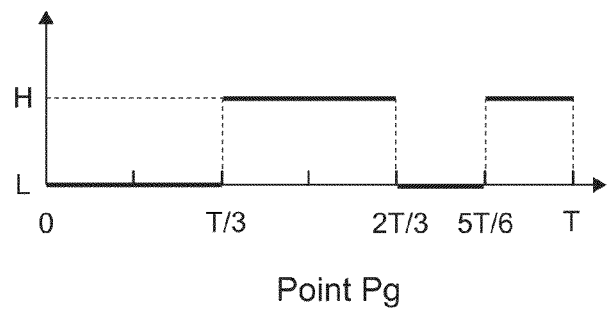
Point Pg
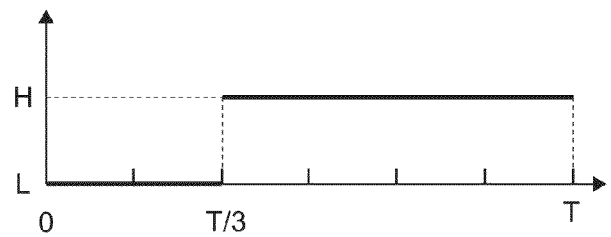
Point Pg'
Stimulation pattern P7 (green)
FIG.26B

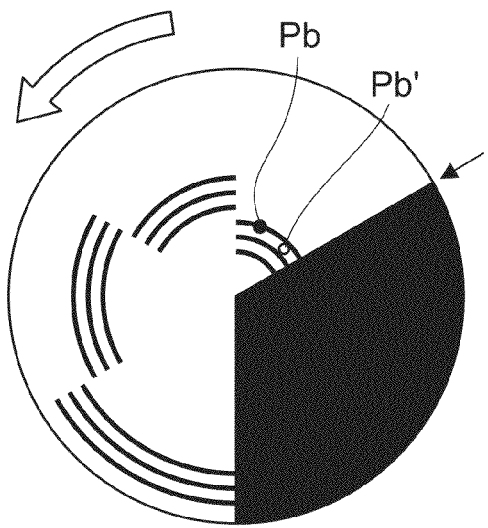
FIG.27A
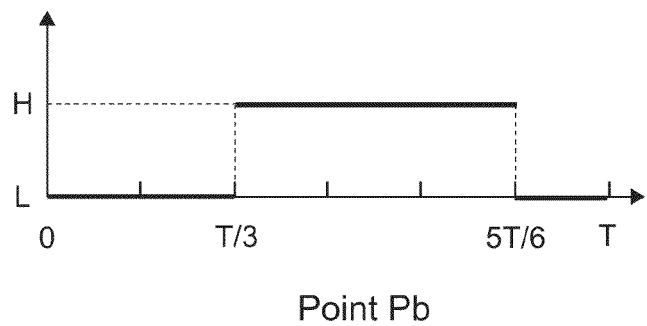
Point Pb
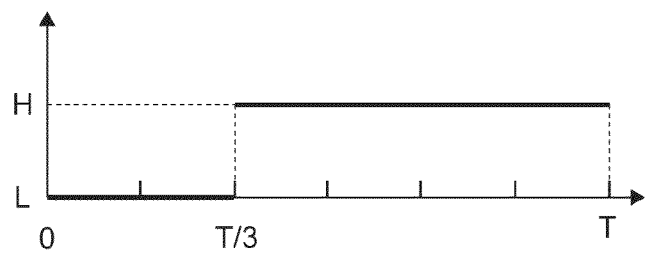
Point Pb'
Stimulation pattern P8 (blue)
FIG.27B

| Presentation color | Corresponding RGB | | | Stimulation pattern |
|---|---|---|---|---|
| | R | G | B | |
| Red "1" | 1 | 0 | 0 | P1 (P5) |
| Green "4" | 0 | 1 | 0 | P3 (P7) |
| Blue "5" | 0 | 0 | 1 | — (P8) |
| Yellow "3" | 1 | 1 | 0 | P2 |
| Orange "2" | 1 | 0.5 | 0.5 | — (P6) |
| Purple "6" | 1 | 0 | 1 | P4 |

VISUAL APPARATUS AND VISUAL METHOD

CROSS REFERENCE TO RELATED APPLICATIONS

This application claims the benefit of Japanese Priority Patent Application JP 2012-241292 filed Oct. 31, 2012, the entire contents of which are incorporated herein by reference.

BACKGROUND

The present disclosure relates to a visual apparatus and a visual method, which support the vision of mainly human beings.

Development of an artificial retina chip and the system thereof has been performed as an aid for mainly those having visual impairments in the past in Germany, Japan, or the like. As the artificial retina chip, a retina chip including a plurality of micro-photodiodes is disclosed in, for example, Subretinal electronic chips allow blind patients to read letters and combine them to words (Proceedings of the Royal SocietyB), 10.1098/rspb.2010.1747 (http://rspb.royalsocietypublishing.org/content/early/2010/11/01/rspb.2010.1747.full) (as of filing date), and a finer retina chip has been produced. The retina chip is configured by integrating the micro-photodiodes and electrodes for outputting electric signals generated by the micro-photodiodes. Specifically, the number of the electrodes is the same as that of the micro-photodiodes, and the electrodes are provided in array. The retina chip is embedded in an eye ball so that the electrodes are brought into contact with the retina.

The artificial visual apparatus disclosed in Japanese Patent Application Laid-open No. 2009-254489 includes a zoom lens, an artificial retina, and a photoelectric conversion apparatus in the stated order from a light incident side. A micro lens array is provided in the photoelectric conversion apparatus (see, for example, paragraph [0008] in the specification of Japanese Patent Application Laid-open No. 2009-254489).

SUMMARY

Even if the number of electrodes in a retina chip is increased and a finer retina chip is produced, the existing apparatus only causes human being to perceive information on up to seven levels of shading of black and white and has a difficulty of causing the human beings to perceive information on color. The reason for this is as follows. The existing retina chip does not cause light having various wavelengths to enter a visual cell of a human being, but applies an electric signal corresponding to information on luminance directly to the visual cell of the human being. Specifically, even if a color filter or the like is mounted on the retina chip, the retina chip obtains information on luminance of 3 areas, i.e., RGB, and the visual cell receives electric signals corresponding to the information on luminance from three electrodes, the human being has a difficulty of perceiving the electric signals as colors.

In view of the circumstances as described above, it is desirable to provide a visual apparatus and a visual method, which are capable of causing mainly human beings to perceive a color.

According to an embodiment of the present disclosure, there is provided a visual apparatus including at least one set of probes and a signal generation unit.

The at least one set of probes includes a plurality of probes.

The signal generation unit generates a stimulation pattern signal corresponding to information on color, and inputs, to at least a part of an area ranging from a retina to a visual nerve, a plurality of pattern signals as the generated stimulation pattern signal via the plurality of probes in the at least one set of probes.

The signal generation unit is capable of causing human beings or animals to perceive a color by inputting, to at least a part of an area ranging from a retina to a visual nerve, the stimulation pattern signals formed by the plurality of pattern signals corresponding to the information on color via the at least one set of probes.

The signal generation unit may generate the stimulation pattern signal for each of different colors. Accordingly, the signal generation unit is capable of causing human beings or animals to perceive a plurality of colors.

The signal generation unit may generate a pair of pattern signals as the plurality of pattern signals, and output each of the pair of pattern signals from at least two proves in the at least one set of probes. Accordingly, it is possible to improve the reproducibility of a color.

Specifically, the at least two probes may be disposed so that one of the pair of pattern signals is input to a center portion of a receptive field of the retina and the other of the pair of pattern signals is input to a peripheral portion of the receptive field of the retina.

More specifically, the signal generation unit may generate a first pattern signal and a second pattern signal as the pair of pattern signals. The first pattern signal includes a pulse having a first duration, and has a predetermined repeated cycle. The second pattern signal includes a pulse having a second duration shorter than the first duration, and has the same repeated cycle as that of the first pattern signal.

The signal generation unit may have, in a case where the repeated cycle is represented by T, a reference clock of T/10 to T/5 for generating the pulse. Accordingly, it is possible to achieve perception of a color by applying a color reproduction phenomenon caused by Benham's top.

The visual apparatus may further include a probe array unit including a plurality of sets of probes as the at least one set of probes. In this case, the plurality of sets of probes of the probe array unit only has to be provided corresponding to a plurality of receptive fields of the retina.

The signal generation unit may select a group of sets of probes disposed at arbitrary positions out of the plurality of sets of probes, and input the stimulation pattern signal. In this case, the signal generation unit may select a group of sets of probes forming arbitrary two-dimensional shape as the group of sets of probes disposed at arbitrary positions.

Alternatively, the signal generation unit may generate a phase difference between the stimulation pattern signals output from the plurality of sets of probes. Accordingly, the reproducibility of the movement of Benham's top is improved. Therefore, the reproducibility of generation of subjective color is improved.

In this case, the signal generation unit may select a group of sets of probes disposed at arbitrary positions out of the plurality of sets of probes, and generate the phase difference between the stimulation pattern signals out of the selected group of sets of probes. Accordingly, it is possible to cause human beings to perceive an image having colors.

The receptive field may be an area in a circle having a diameter of not less than 1 μm and not more than 30 μm.

The signal generation unit may generate a signal having a repeated cycle of not less than 3.5 Hz and not more than 10 Hz as the stimulation pattern signal.

The signal generation unit may generate one of an electric signal and an optical signal as the stimulation pattern signal.

According to an embodiment of the present disclosure, there is provided a visual method, including generating a stimulation pattern signal corresponding to information on color, the stimulation pattern signal including a plurality of pattern signals.

The plurality of pattern signals are input to at least a part of an area ranging from a retina to a visual nerve via a plurality of probes included in at least one sets of probes.

As described above, according to the present disclosure, it is possible to cause mainly human beings to perceive a color.

These and other objects, features and advantages of the present disclosure will become more apparent in light of the following detailed description of best mode embodiments thereof, as illustrated in the accompanying drawings.

BRIEF DESCRIPTION OF DRAWINGS

FIGS. 2A to 2D are diagrams for explaining an operation of the receptive field;

FIG. 6A is a diagram for explaining a change in light and dark (black and white) in an area of stripes in which the subjective color of red is generated when the Benham's top is rotated, and FIG. 6B shows a time change in the light and dark;

FIG. 7A is a diagram for explaining a change in light and dark (black and white) in an area of stripes in which the subjective color of yellow is generated, and FIG. 7B shows a time change in the light and dark;

FIG. 8A is a diagram for explaining a change in light and dark (black and white) in an area of stripes in which the subjective color of green is generated, and FIG. 8B shows a time change in the light and dark;

FIG. 9A is a diagram for explaining a change in light and dark (black and white) in an area of stripes in which the subjective color of purple is generated, and FIG. 9B shows a time change in the light and dark;

FIG. 13 shows a plurality of examples of arrangement of the electrode in a receptive field having the size larger than that of the receptive field according the embodiment shown in FIG. 12;

FIG. 17B shows, in the embodiment in which a set of electrodes is arranged for each receptive field in a honeycomb pattern shown in FIG. 17A, an electrical stimulation pattern signal input to the receptive field;

FIG. 18A shows an example in which sets of electrode arranged in receptive fields on vertical lines shown in FIG. 18A are driven in synchronization in two top patterns shown in FIG. 18B;

FIG. 19A shows a predetermined area to be selected in a plurality of receptive areas, and FIGS. 19B and 19C each show an example in which electrical stimulation pattern signals that are different between the selected area and the other areas are input;

FIGS. 24A and 24B show another example of Benham's top for explaining generation of the subjective color of red;

FIGS. 25A and 25B show another example of Benham's top for explaining generation of the subjective color of orange;

FIGS. 26A and 26B show another example of Benham's top for explaining generation of the subjective color of green;

FIGS. 27A and 27B show another example of Benham's top for explaining generation of the subjective color of blue;

DETAILED DESCRIPTION OF EMBODIMENTS

Hereinafter, embodiments according to the present disclosure will be described with reference to the drawings.

1. Structure and Function of Retina

Figure 1:
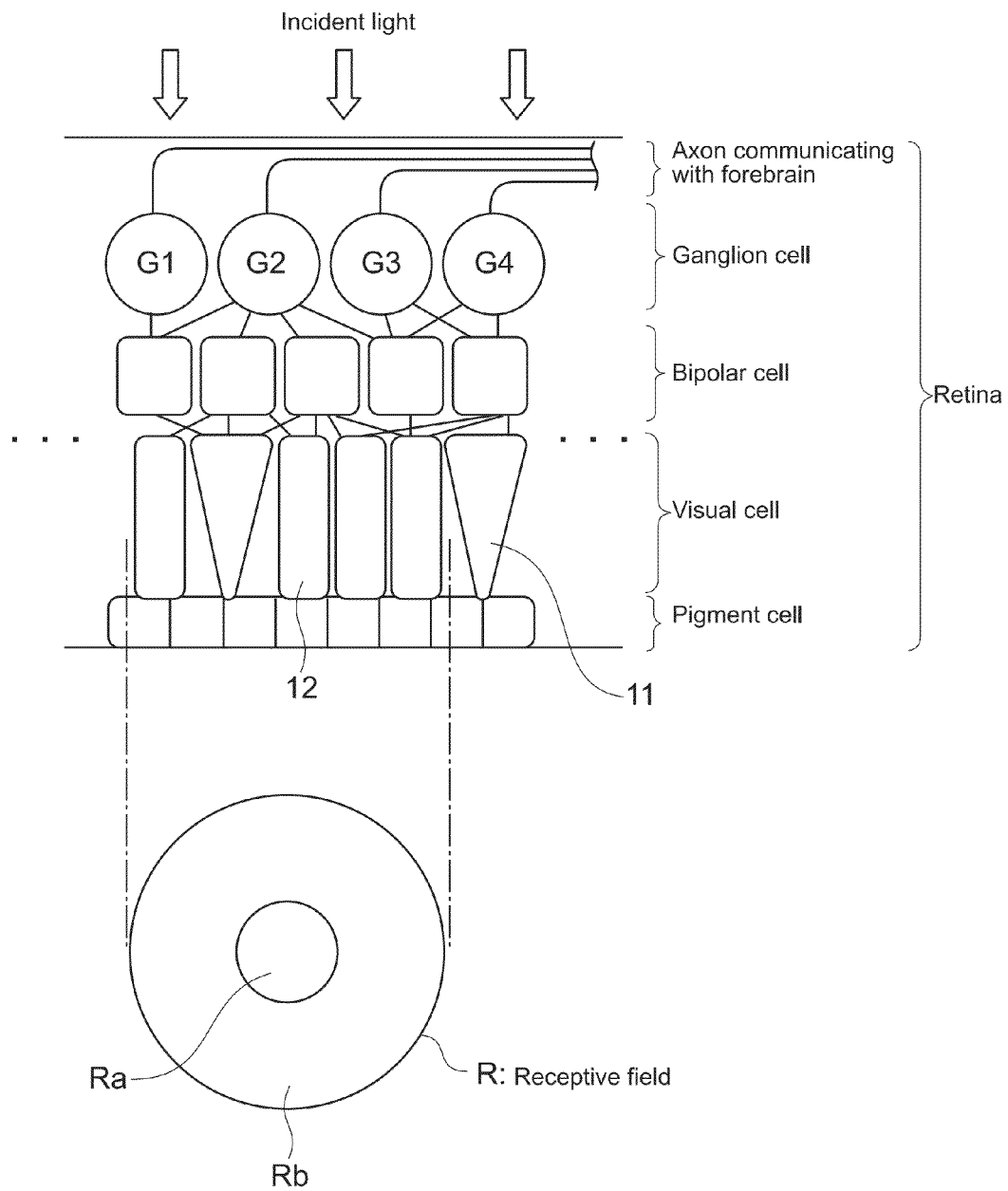
FIG. 1 is a diagram schematically and conceptually showing a cross-sectional structure of a retina of a human being.

The upper portion of FIG. 1 schematically and conceptually shows a cross-sectional structure of a retina of a human being. The retina includes a ganglion cell, a bipolar cell, a visual cell, and a pigment cell in the stated order from a light incident side. In addition to the shown bipolar cell, a horizontal cell, an amacrine cell, and the like, which are not shown, exist between the ganglion cell and the visual cell. The side on which the pigment cell exists is a back side of the retina.

The bipolar cell communicates with one or more (n) visual cells. The ganglion cell communicates with one or more (m) bipolar cells. Here, an area where (n×m) visual cells that communicate with one ganglion cell exist is a receptive field in a visual system. The receptive field has a function to detect contrast, i.e., is defined as a functional area for detecting an edge of an object.

The lower portion of FIG. 1, which is a plan view, shows one receptive field R drawn to have a circular shape and a size corresponding to one ganglion cell G2.

Most of the receptive filed is configured by a lot of visual cells (including a pyramidal cell 11 and a rod cell 12). In the plane of the retina, because the ganglion cells, the bipolar cells, and the visual cells correspond to (communicate with) each other at a ratio of close to 1:1 at a center portion of the retina, the diameter of the receptive filed is relatively small. On the other hand, because one ganglion cell corresponds to (communicate with) a lot of bipolar cells and visual cells in the periphery of the retina, the diameter of the receptive field is relatively large.

It should be noted that a human being has 1.2 million to 1.5 million ganglion cells, and about 100 million visual cells. In the case of a human being, the n×m is several thousand.

Information on incident light first enters a visual cell. The visual cell converts received light into an electric signal being a neural signal. A ganglion cell transmits the information to a forebrain via a bipolar cell and the like by an electric signal from a visual cell. A pigment cell is a cell that makes a wall on the outside of a retina.

As sown in FIG. 1, the receptive field R is configured by a center area Ra and a surrounding area Rb surrounding the center area Ra, which are functionally apart, in order to fulfill the above-mentioned function to detect an edge. This is particularly called "antagonistic center-surround type receptive field." FIGS. 2A to 2D are diagrams for explaining the operation of the receptive field. Examples of the receptive field include an on-center receptive field shown in FIGS. 2A and 2B, and an off-center receptive field shown in FIGS. 2C and 2D.

As shown in FIG. 2A, the on-center receptive field shows a relatively strong response (generates an active potential ("firing and excitation")) in the case where only the center area Ra thereof receives light, and transmits the signal to a ganglion cell via a bipolar cell and the like. As shown in FIG. 2B, the on-center receptive field shows no response in the case where only the surrounding area Rb receives light. On the other hand, as shown in FIGS. 2C and 2D, the off-center receptive field shows a relatively strong response in the case where only the surrounding area Rb receives light, and shows no response in the case where only the center area Ra receives light. The strength of the response depends on the amount of received light.

It should be noted that the on-center and off-center receptive fields show a relatively weak response or no response in the case where no contrast of light exists between the center area Ra and the surrounding area Rb. The case where no contrast of light exists between the center area Ra and the surrounding area Rb is, specifically, a case where light is incident on the center area Ra and the surrounding area Rb or a case where no light is incident thereon.

2. Configuration Example of System

Figure 3:
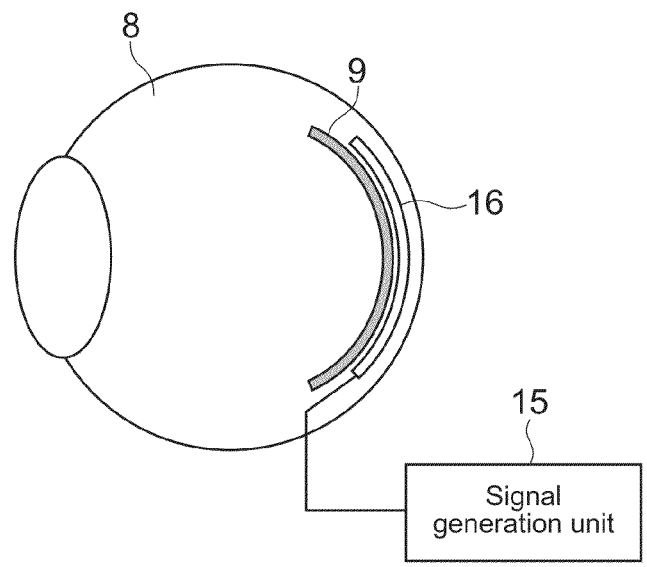
FIG. 3 shows a system using a visual apparatus according to an embodiment of the present disclosure.
Figure 4:
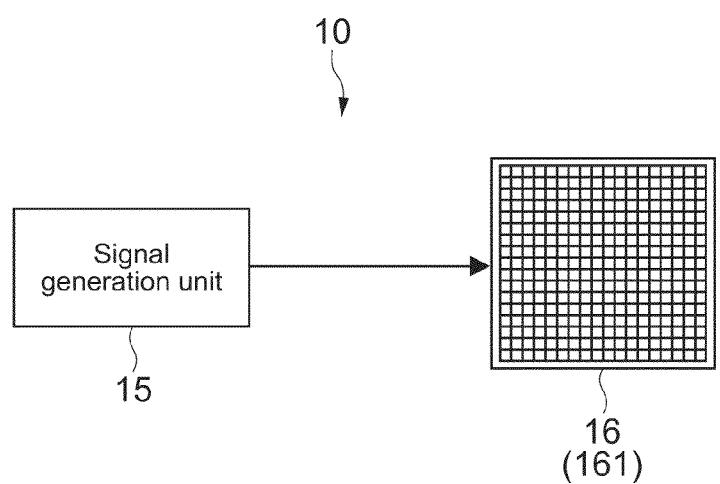
FIG. 4 shows the configuration of the visual apparatus.

FIG. 3 shows a system using a visual apparatus according to an embodiment of the present disclosure. FIG. 4 shows a configuration of a visual apparatus 10. The visual apparatus 10 includes a retina chip 16 provided in an eye ball 8, a signal generation unit 15 electrically connected to the retina chip 16.

The retina chip 16 is an electrode array unit 161 (probe array unit) mounted on the side of a visual cell, which is the outside of a retina 9, for example. The electrode array unit 161 typically includes a plurality of electrodes in horizontal and vertical directions, i.e., includes a plurality of electrodes arranged in a matrix pattern. To each electrode, a voltage signal generated by the signal generation unit 15 is individually applied. In this case, the individual electrode functions as a probe.

The size of the retina chip 16 is, for example, 3 mm squares, and the thickness thereof is 4 to 15 μm. However, the retina chip 16 is not limited to such sizes. As the material of the electrode, metal that has a difficulty in reacting with a biological tissue, such as platinum, is used.

The signal generation unit 15 is achieved by a hardware element used in a computer such as CPU (Central Processing Unit), RAM (Random Access Memory), and ROM (Read Only Memory), and software. Alternatively, the signal generation unit 15 may be achieved by PLD (Programmable Logic Device) such as FPGA (FieldProgrammable Gate Array), or devices such as ASIC (Application Specific Integrated Circuit).

With such a configuration of the visual apparatus 10, the signal generation unit 15 is capable of inputting an electric signal having a predetermined pattern generated as described later to the retina 9 via each electrode of the retina chip 16.

Figure 5:
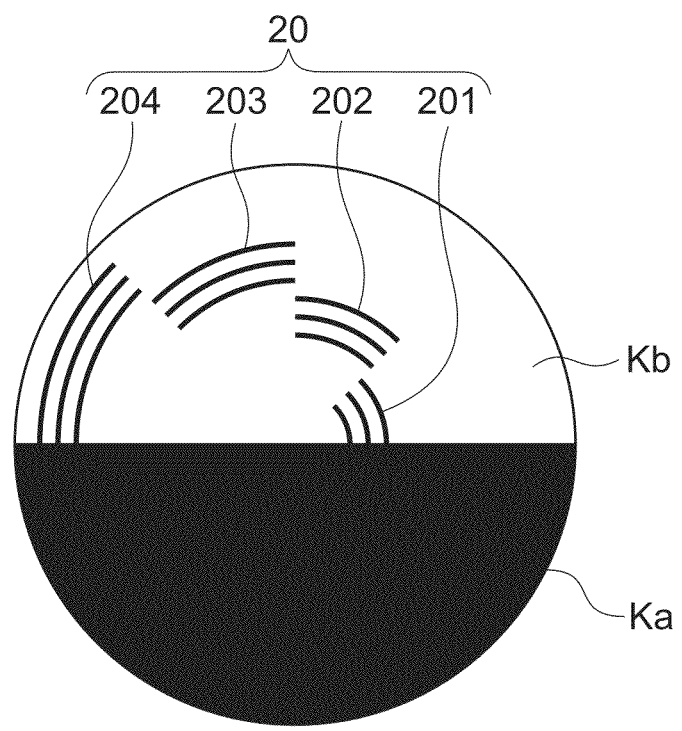
FIG. 5 is a plan view showing Benham's top.

3. Principle of Perception of Color by Visual Apparatus (1) Principle of Generation of Subjective Color by Benham's Top Next, a principle of perception of a color by a system using the visual apparatus 10 according to this embodiment will be described. FIG. 5 is a plan view showing Benham's top.

In the Benham's top, basically, an area Ka having a rotational angle of 180° is blacked out, and black-on-white stripes 20 are drawn in an area Kb having a rotation angle of 180° positioned on the opposite side. Specifically, in the area Kb, a set of stripes 20 including three circular arcs is drawn for each of areas having a rotational angle of 45° obtained by dividing the area Kb into four areas at different radial positions. Specifically, the stripes 20 include four kinds of stripes 201, 202, 203, and 204).

In FIG. 5, when the Benham's top is rotated clockwise, it is seen that colors of red, yellow, green, and purple are generated from a side having a small radius, i.e., inside, in each of the areas of stripes 201, 202, 203, and 204. The black color of the area Ka and the stripes 20 are alternately presented, and thus such a subjective color is generated. It is considered that the subjective color is generated by periodically repeating the passage through the center area Ra and the surrounding area Rb of the receptive field R and stationary state of a ganglion cell by the area Ka in view of the shape of the above-mentioned antagonistic center-surround type receptive field. Moreover, although there is considered to be an individual difference, each color is most brilliantly generated when the Benham's top is rotated at a rate of 7 rotation/sec, i.e., at a rotation frequency of 7 Hz (cycle T=0.143 seconds). The rotation frequency is not limited to 7 Hz, and the Benham's top is favorably rotated at 3.5 to 10 Hz (cycle T=0.1 to 0.28 seconds) in this embodiment.

The visual apparatus 10 according to this embodiment uses such a phenomenon of generation of the subjective color by the Benham's top to generate a stimulation pattern signal by electricity in the following way.

FIG. 6A is a diagram for explaining a change in light and dark (black and white) in an area of stripes 201 in which the subjective color of red is generated when the Benham's top is rotated. FIG. 6B shows a time change in the light and dark (stimulation pattern P1).

As shown in FIG. 6A, a point Pr is a point through which circular arc lines forming the stripes 201 pass. A point Pr' is a point through which white area between the circular arc lines passes. The change in light and dark on the point Pr, i.e., change in light and dark on the line along circles at a radial position of the point Pr, corresponds to the bottom pattern shown in FIG. 6B.

In FIG. 6B, L represents a dark (black) state, and H represents a light (white) state. The Benham's top rotates clockwise, and a position of a rotational angle represented by a black arrow in FIG. 6A is a position of time t=0. A reference clock of time is ⅛ of one cycle (1 rotation).

The patterns shown in FIG. 6B can be represented by the following formulae 1 and 2.

$$\text{Point } Pr: \lambda_{pr}(t)=L(0 \le t<5T/8), H(5T/8 \le t<T) \quad \text{Formula 1}$$

$$\text{Point } Pr': X_{pr}'(t)=L(0 \le t<T/2), H(T/2 \le t<T) \quad \text{Formula 2}$$

Similarly to this, FIGS. 7, 8, and 9 show radial positions on the Benham's top and changes in light and dark for each radial position when the subjective colors of yellow, green, and purple are generated, respectively. Typical points at the radial positions are represented by Py and Py' in FIGS. 7A and 7B, Pg and Pg' in FIGS. 8A and 8B, and Pp and Pp' in FIGS. 9A and 9B.

Moreover, similarly to the above-mentioned formulae 1 and 2, stimulation patterns P2, P3, and P4 shown in FIGS. 7B, 8B, and 9B, respectively, can be represented by the following formulae 3 to 8.

$$\text{Point } Py: X_{py}(t)=L(0 \le t<T/2), L(5T/8 \le t<3T/4), H(T/2 \le t<5T/8), H(3T/4 \le t<T) \quad \text{Formula 3}$$

$$\text{Point } Py': X_{py}'(t)=L(0 \le t<T/2T), H(T/2T \le t<T) \quad \text{Formula 4}$$

$$\text{Point } Pg: X_{pg}(t)=L(0 \le t<T/2), L(3T/4 \le t<7T/8), H(T/2 \le t<3T/4), H(7T/8 \le t<T) \quad \text{Formula 5}$$

$$\text{Point } Pg': X_{pg}'(t)=L(0 \le t<T/2), H(T/2 \le t<T) \quad \text{Formula 6}$$

$$\text{Point } Pp: X_{pp}(t)=L(0 \le t<T/2), L(7T/8 \le t<T), H(T/2 \le t<7T/8) \quad \text{Formula 7}$$

$$\text{Point } Pp': X_{pp}'(t)=L(0 \le t<T/2), H(T/2 \le t<T) \quad \text{Formula 8}$$

In order to maintain such perception of colors for more than a predetermined time period, it is favorable not to stop stimulation at one cycle, but to repeat the stimulation. Such reputation of stimulation is one of the characteristics of the present disclosure. Moreover, as will be described later, it is also one of the characteristics of the present disclosure that stimulation pattern is changed on the retina to switch perception of colors.

The visual apparatus 10 according to this embodiment can generate subjective colors by inputting pairs of pattern signals, which are represented by the formulae (1 and 2), (3 and 4), (5 and 6), and (7 and 8), to the receptive field of the retina as stimulation pattern signals by electricity as described above.

It should be noted that although the rotation direction of the above-mentioned Benham's top has been described as a clockwise rotation, subjective colors are generated even in the case of a counterclockwise rotation, of course.

(2) Example of Arrangement of Electrode

Next, an example of arrangement of the electrode of the electrode array unit 161 for inputting signals of the stimulation patterns P1 to P4 to the receptive field will be described.

(A) Arrangement of Electrode with Respect to One Receptive Field

Figure 10:
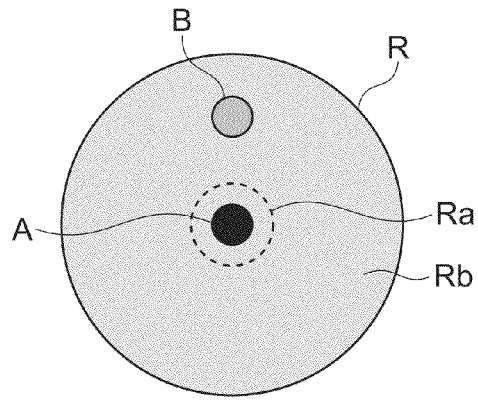
FIG. 10 shows an example of arrangement of an electrode with respect to one receptive field.

FIG. 10 shows an example of arrangement of an electrode with respect to one receptive field R. In this embodiment, a set of electrodes (set of probes) including a plurality of electrodes (A and B) corresponds to the receptive filed R. In this example, out of the set of electrodes A and B, the electrode A is arranged in the center area Ra of the receptive field R, and the electrode B is arranged in the surrounding area Rb. For example, the electrode A inputs one of the electrical stimulation pattern signals of the points Pr, Py, Pg, and Pp, which are shown in FIGS. 6B, 7B, 8B, and 9B, respectively. The electrode B inputs one of the electrical stimulation pattern signals of the points Pr', Py', Pg', and Pp', which are shown in FIGS. 6B, 7B, 8B, and 9B, respectively. Alternatively, the electrodes A and B may be replaced with each other.

It should be noted that the electrodes may be arranged any of an on-center receptive field and an off-center receptive field.

Formulae 1' to 8' of electrical stimulation pattern signals (e.g., current signals) by the set of electrodes (A and B), which correspond to the above-mentioned formulae 1 to 8, respectively, are shown in the following. I represents an amplitude corresponding to a current signal, and A represents an amplitude corresponding to an H level. Units of them are ampere and joule.

$$\text{Electrode } A: I_{ar}(t)=\{0(0 \le t<5T/8), A(5T/8 \le t<T)\} \quad \text{Formula 1'}$$

$$\text{Electrode } B: I_{br}'(t)=\{0(0 \le t<T/2), A(T/2 \le t<T)\} \quad \text{Formula 2'}$$

$$\text{Electrode } A: I_{ay}(t)=\{0(0 \le t<T/2), 0(5T/8 \le t<3T/4), A(T/2 \le t<5T/8), A(3T/4 \le t<T)\} \quad \text{Formula 3'}$$

$$\text{Electrode } B: I_{by}'(t)=\{0(0 \le t<T/2), A(T/2 \le t<T)\} \quad \text{Formula 4'}$$

$$\text{Electrode } A: I_{ag}(t)=\{0(0 \le t<T/2), 0(3T/4 \le t<7T/8), A(T/2 \le t<3T/4), A(7T/8 \le t<T)\} \quad \text{Formula 5'}$$

$$\text{Electrode } B: I_{bg}'(t)=\{0(0 \le t<T/2), A(T/2 \le t<T)\} \quad \text{Formula 6'}$$

$$\text{Electrode } A: I_{ap}(t)=\{0(0 \le t<T/2), 0(7T/8 \le t<T), A(T/2 \le t<7T/8)\} \quad \text{Formula 7'}$$

$$\text{Electrode } B: I_{bp}'(t)=\{0(0 \le t<T/2), A(T/2 \le t<T)\} \quad \text{Formula 8'}$$

The pattern represented by the formulae 2', 4', 6', and 8' functions as a first pattern signal. Moreover, the pattern represented by the formulae 1', 3', 5', and 7' functions as a second pattern signal. Specifically, the first pattern signal includes a pulse having a first duration and a predetermined repeated cycle. On the other hand, the second pattern signal includes a pulse having a second duration shorter than the first duration and the same repeated cycle T as that of the first pattern signal.

Figure 11:
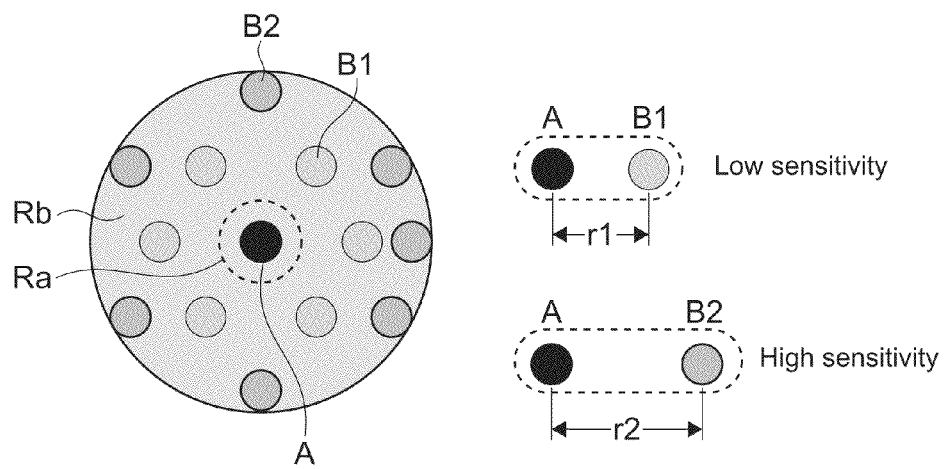
FIG. 11 shows an example in which a plurality of electrodes are arranged in a peripheral portion of the receptive field.

As shown in FIG. 11, a plurality of electrodes B (B1 and B2) may be arranged in the surrounding area Rb of the receptive field. In this case, the plurality of electrodes B input the above-mentioned stimulation pattern signal to the surrounding area Rb of the receptive field in a coordinate phase. As the number of electrodes B increases, the signal gets stronger.

In the example shown in FIG. 11, the electrodes B1 are arranged at positions away from the electrode A arranged in the center area Ra of the receptive field by a distance r1, and the electrodes B2 are arranged at positions away from the electrode A by a distance r2 greater than r1. In the case where only the set of electrodes (A and B) is considered, it has been found that the sensitivity (output) of a receptive field of a human being with respect to the stimulation pattern signal input by the set of electrodes (A and B1) is lower than that input by the set of electrodes (A and B2). Therefore, by adjusting the distance between the set of electrodes (A and B), it is possible to adjust the sensitivity.

Here, the area of the receptive field is an area having an angle of approximately 30 seconds to 10 minutes as a field of view. Moreover, the diameter of the receptive field is approximately 1 to 30 μm.

Figure 12:
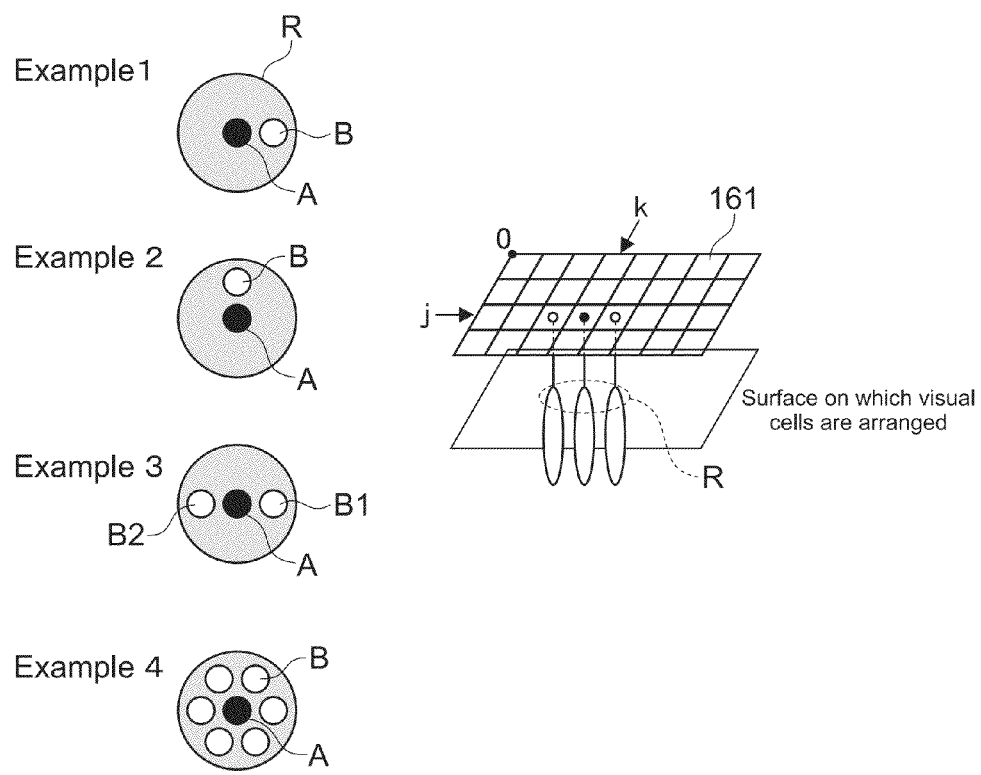
FIG. 12 shows a plurality of examples of arrangement of a set of electrodes in the case where the diameter of the receptive field is the same as the size of three visual cells.

FIG. 12 shows a plurality of examples of arrangement of a set of electrodes in the case where the diameter of the receptive field R is the same as the size of three visual cells (4.5 to 6 μm), for example. A case where one electrode B is arranged is shown in examples 1 and 2, and a case where a plurality of electrodes B are arranged is shown in examples 3 and 4. On the right of FIG. 12, a relationship between arrangement of electrodes of the electrode array unit 161 and visual cells of the receptive field R is shown. The right of FIG. 12 corresponds to the example 3. Coordinate pairs of the electrodes according to the embodiments shown in examples 1, 2, and 3 are shown in the following.

Example 1 electrode A(k, j), electrode B(k+1, j)

Example 2 electrode A(k, j), electrode/B(k, j+1)

Example 3 electrode A(k, j), electrode B1(k+1, j), electrode B2(k−1, j)

FIG. 13 shows a plurality of examples of arrangement of the electrode in a receptive field having the size larger than that of the receptive field according the embodiment shown in FIG. 12, e.g., a diameter of 9 visual cells. Coordinate pairs of the electrodes according to the embodiments shown in the examples 4, 5, and 6 in FIG. 13 are shown in the following.

Example 5 electrode A(k, j), electrode B(k+3, j)

Example 6 electrode A1(k, j), electrode A2(k+1, j), electrode A3(k−1, j), electrode B1(k+2, j), electrode B2(k−2, j)

Example 7 electrode A(k, j), electrode B1(k+1, j), electrode B2(k+2, j), electrode B3(k−1, j), electrode B4(k−2, j)

(B) Arrangement of Electrodes with Respect to Plurality of Receptive Field

Next, examples of arrangement of electrodes with respect to a plurality of receptive fields R arranged in predetermined positions will be described as a more realistic embodiment than the case of the above-mentioned (A). Also in this case, the embodiment in which a set of electrodes (two or more electrodes) corresponds to one receptive field is followed. Moreover, in the following description, an embodiment in which a set of two electrodes (A and B) is arranged with respect to one respective field R will be described. However, it is needless to say that the present disclosure can be applied to an embodiment in which a set of three or more electrodes (see, for example, examples 3 and 4 in FIG. 12, and examples 6 and 7 in FIG. 13) are arranged with respect to one respective field.

Figure 14:
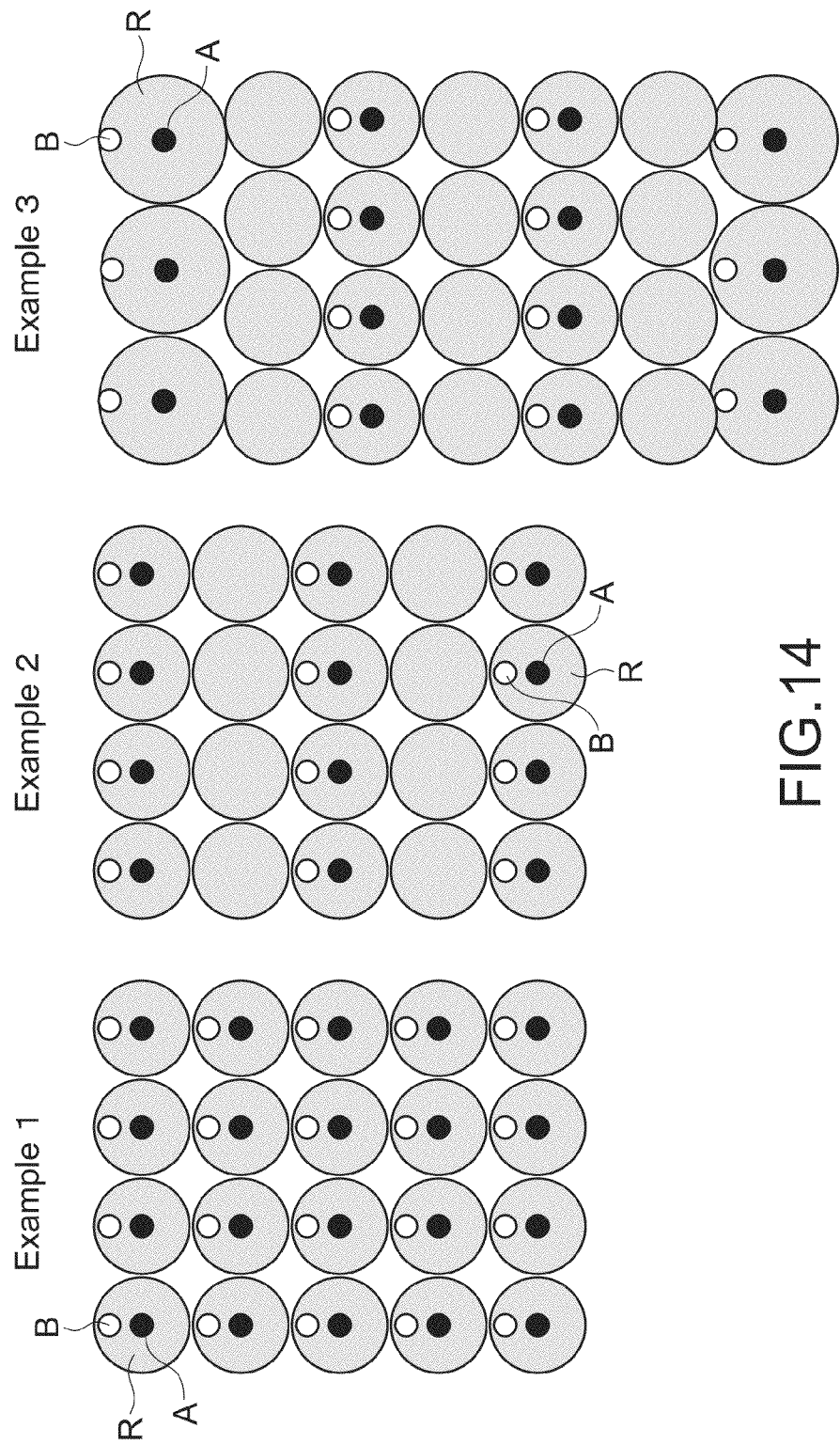
FIG. 14 shows examples of arrangement of the electrode in the case where receptive fields are arranged in a matrix pattern.

FIG. 14 shows examples of arrangement of the electrode in the case where the receptive fields R are arranged in a matrix pattern.

Example 1

In this example, a set of electrodes is arranged in each receptive field.

Example 2

In this example, a set of electrodes is arranged in the receptive field R in every predetermined rows (or every predetermined columns), i.e., in every two rows in the example 2 in FIG. 14.

Example 3

Normally, the receptive field R having a relatively small size is provided on the center side of the retina, and the receptive field R having a relatively large size is provided on the surrounding side of the retina. In the example 3, the electrode array unit 161 including a plurality of electrodes arranged in a matrix pattern, in which the distance between the set of electrodes (A and B) is set, is designed depending on such a size of the receptive field.

Figure 15:
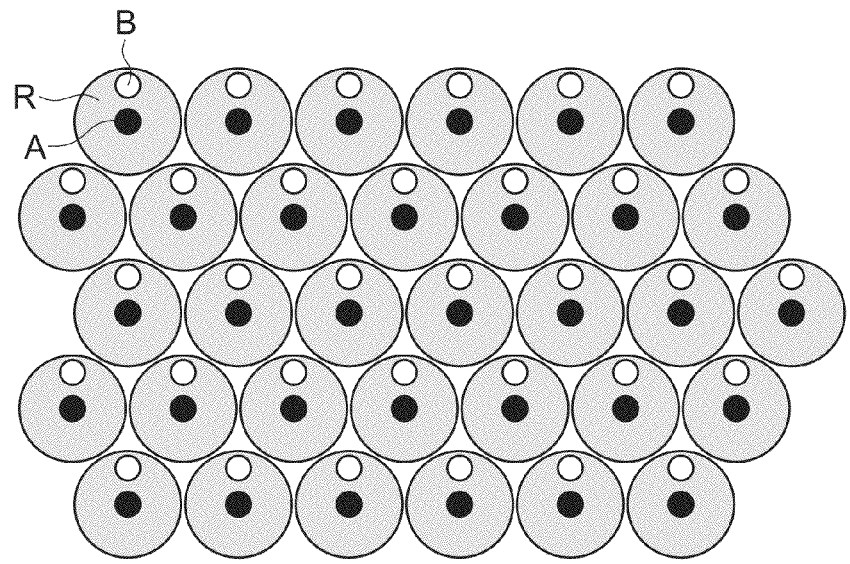
FIG. 15 shows an example in which receptive fields are arranged in a honeycomb pattern.

FIG. 15 shows an example in which the set of electrodes (A and B) is provided for each receptive field R, which is arranged in a honeycomb pattern. Specifically, the electrode array unit 161 is designed so that each electrode of the electrode array unit 161 is arranged in a honeycomb pattern.

Figure 16:
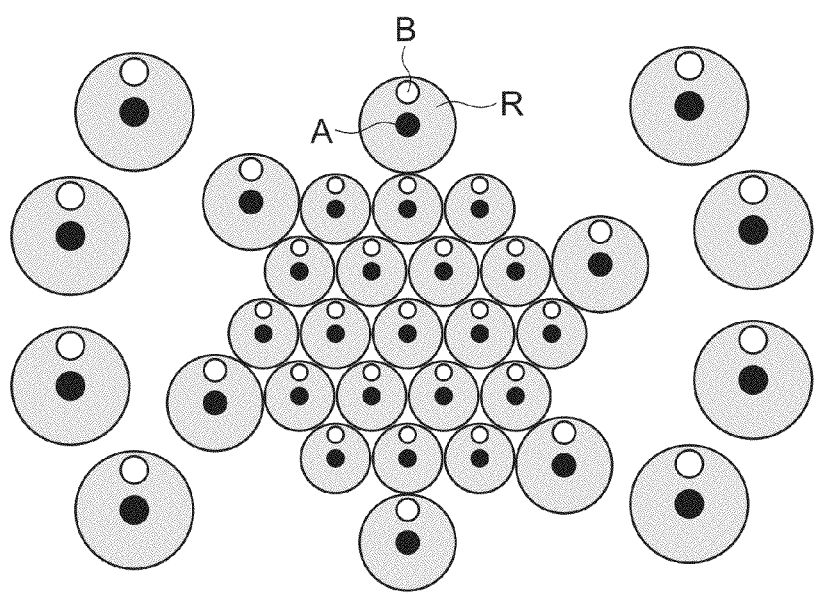
FIG. 16 shows an example in which receptive fields having different sizes are arranged in a honeycomb pattern.

FIG. 16 shows an example in which the receptive fields R are arranged in a honeycomb pattern and, the set of electrodes (A and B) are provided for each receptive field in the case where the retina includes the receptive fields having different sizes as described above. As described above, because the size of the receptive field decreases towards the center of the retina and increases towards the surrounding area of the retina, it is favorable to arrange the set of electrodes (A and B) depending on the size of the receptive field.

Although examples of arrangement of the electrode have been described, all of the set of electrodes of the electrode array unit 161 do not necessarily correspond to the receptive fields, as shown in FIGS. 14 to 16. More realistically, it only has to arrange a part of the electrodes as shown in FIGS. 14 to 16 when the electrode array unit 161 is mounted on the retina.

It should be noted that the set of electrodes (A and B) may be arranged for every predetermined rows or columns as in the case of the concept of the example 2 or 3 shown in FIG. 14, for example, with respect to the receptive fields R provided in a honeycomb pattern as shown in FIG. 15.

Next, a method of driving an electrical stimulation pattern signal by the signal generation unit 15 in the case where the set of electrodes are arranged in a plurality of receptive fields will be described. In describing the driving method, the description will be made in two parts, i.e., a case where electrical stimulation pattern signals from a plurality of electrodes are all in a coordinate phase (a) and a case where the electrical stimulation pattern signals have phase differences (3).

(α) Case where Electrical Stimulation Pattern Signals are in Coordinate Phase

FIG. 17B shows electrical stimulation pattern signals input to the receptive fields in the embodiment in which the set of electrodes is arranged for each receptive field arranged in a honeycomb pattern as shown in FIG. 17A. In this example, the cycle T=0.143 seconds, and a reference clock (tick) is T/6=0.024 seconds as will be described later.

FIG. 18A shows an example in which the set of electrodes (A and B) arranged in the receptive fields R located on the vertical lines in FIG. 18A are driven in synchronization in two top patterns shown in FIG. 18B (the same pattern as that shown in FIG. 17B, in this example). A signal input to the set of electrodes (A and B) arranged in the receptive fields R other than those located on the vertical lines has an unchanged DC (direct current) (or zero) value. As described above, the signal generation unit 15 is capable of selecting arbitrary target sets of electrodes out of all of the sets of electrodes, i.e., a group of sets of electrodes arranged at arbitrary positions, and driving them.

In particular, as shown in FIGS. 19A and 19B, the signal generation unit 15 is capable of also selecting a group of sets of probes corresponding to the receptive fields R that form an arbitrary two-dimensional shape surrounded by a thick alternate long and short dash line M, and driving them. If the two-dimensional shape includes a lot of receptive fields and forms a predetermined shape, it is possible to cause human beings to perceive an image of a character, a graphic, or the like, which has a color.

Alternatively, as shown in FIG. 19C, the signal generation unit 15 may select sets of electrodes corresponding to areas other than the area surrounded by the thick alternate long and short dash line M, and input the electrical stimulation pattern signal. Specifically, by exclusively processing signals of the sets of electrodes corresponding to the area surrounded by the thick alternate long and short dash line M without changing the signals, the signal generation unit 15 is capable of causing human beings to perceive a shape formed by areas that are not stimulated.

The method of selecting a group of sets of electrodes arranged at arbitrary positions and driving them described above can be applied also to the arrangement of the receptive fields R shown in the examples 2 and 3 in FIG. 14, or in FIG. 16. Specifically, the signal generation unit 15 may select a group of sets of electrodes corresponding to the target receptive fields out of all of the receptive fields shown in the figures and driving them.

(β) Case where Stimulation Pattern Signal has Phase Difference

Figure 20A:
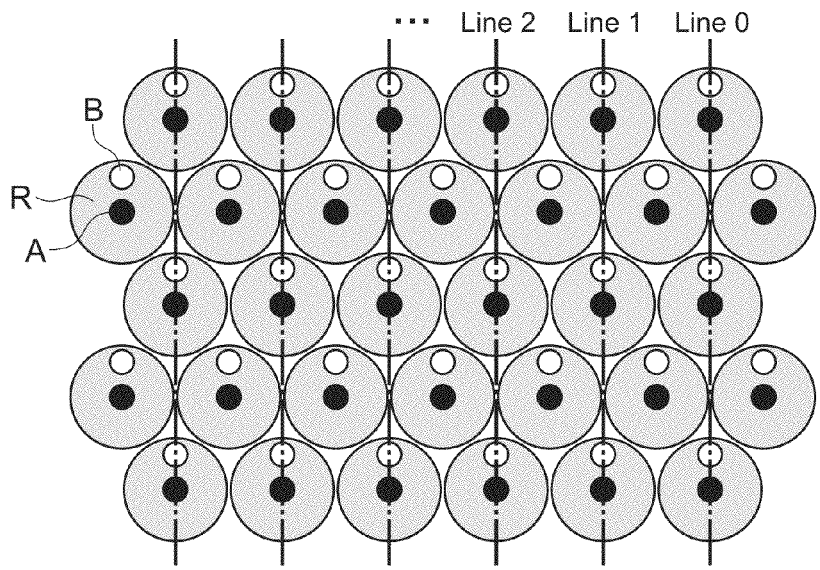
FIGS. 20A and 20B each show an exemplary electrical stimulation pattern having a phase difference for each area on the retina.
Figure 20B:
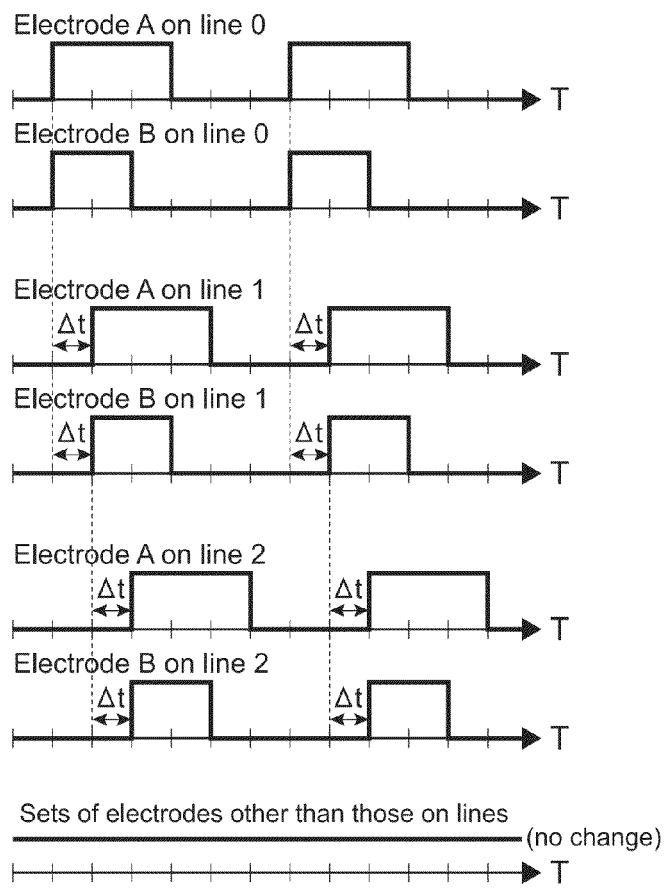

FIGS. 20A and 20B show an example in which an electrical stimulation pattern signal having a phase difference for each region on the retina is generated. For example, as shown in FIG. 20A, an electrical stimulation pattern signal having a phase difference (Δt) is generated for each set of electrodes (A and B) arranged on the receptive fields R located on lines 0, 1, 2, . . . , out of the receptive fields R arranged in a honeycomb pattern. With such a scanning process, it is possible to reproduce a phenomenon such that the movement of the Benham's top is projected to the retina, and to improve the reproducibility of generation of the subjective color.

The distance between electrodes to be scanned is represented by ΔX, and the scanning rate on the electrode array, i.e., the progression rate of the pulse of the electrical stimulation pattern signal is represented by V. The signal generation unit 15 can set a phase difference in an amount correspond to a time period for progressing in the X direction (ΔX/V) divided by a cycle T (s), for example. Therefore, the electrical stimulation pattern signal applied to electrodes C and D (illustration is omitted), which are away from each other by a predetermined distance ΔX in the X direction, of the above-mentioned electrodes A and B (electrodes to which the electrical stimulation pattern signal represented by the formulae 1' and 2' is applied) is represented by the following formulae 1'' and 2''.

Electrode C: $I_{cr}(t)=\{0(0 \le t-\Delta X/V<5T/8), A(5T/8 \le t-\Delta X/V<T)\}$     Formula 1''

Electrode D: $I_{dr}'(t)=\{0(0 \le t-\Delta X/V<T/2), A(T/2 \le t-\Delta X/V<T)\}$     Formula 2''

By performing such a scanning process on a group of electrodes in an arbitrary shape covering an area larger than one receptive field R to stimulate the retina, the signal generation unit 15 is capable of causing human beings to perceive a red area having the arbitrary shape, i.e. an image having the subjective color of red.

It should be noted that the formulae 1'' and 2'' represent a signal for generating the subjective color of red. However, it is needless to say that the signal generation unit 15 may generate signals for generating other subjective colors corresponding to the above-mentioned formulae 3' to 8', similarly.

By developing the technique shown in FIG. 20, the signal generation unit 15 may select a group of sets of electrodes arranged in the receptive fields R corresponding to the arbitrary two-dimensional shape, and generate a phase difference between electrical stimulation patterns input via the selected group of sets of electrodes. For example, a stimulation pattern of the retina by the group of sets of electrodes at a given time is shown in FIG. 21.

Figure 21:
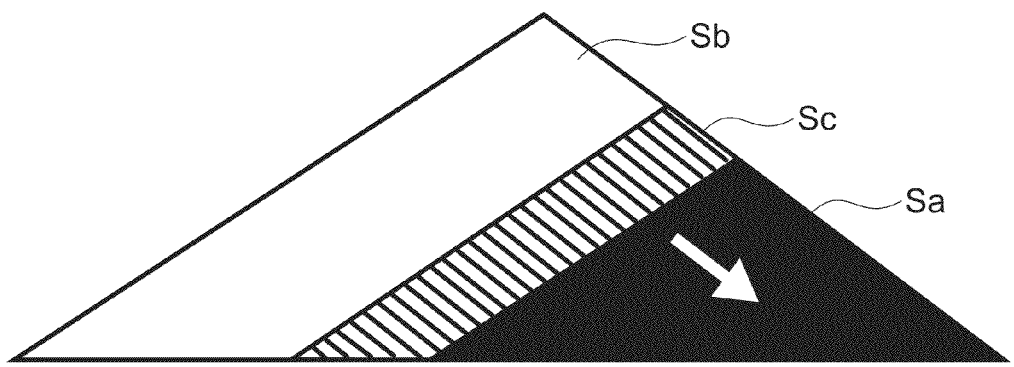
FIG. 21 shows a stimulation pattern of the retina caused in a predetermined area on the retina by a group of sets of electrodes at a given time.

In FIG. 21, a triangular shape is set as the arbitrary two-dimensional shape, for example, and a pulse of an electrical stimulation pattern signal progresses in a direction of a white arrow in the triangular shape. In this case, a black portion Sa in the triangular shape corresponds to, for example, a black portion Ka in the Benham's top, and a white portion Sb corresponds to a white portion Kb in the Benham's top. Then, stripes Sc in the triangular shape correspond to the stripes 20 in the Benham's top. Here, if the frequency of the repeated cycle of the electrical stimulation pattern signal is 3.5 to 10 Hz as described above, it is possible to improve the reproducibility of the movement of the Benham's top, and to improve the reproducibility of generation of the subjective color in an arbitrary two-dimensional shape.

If a pulse length of one cycle of an electrical stimulation pattern signal is represented by L, the area of the black area of the triangular shape shown in FIG. 21 is a part of the entire area of the triangular shape (e.g., about ¼). Therefore, the signal generation unit 15 may scan the target set of electrodes on the retina at the rate V satisfying the following formula 9.

$V/L=3.5\sim10$     Formula 9

Next, as another example of arrangement of electrodes with respect to a plurality of receptive fields, a case where the receptive fields are spatially overlaid one on the other will be described.

Figure 22:
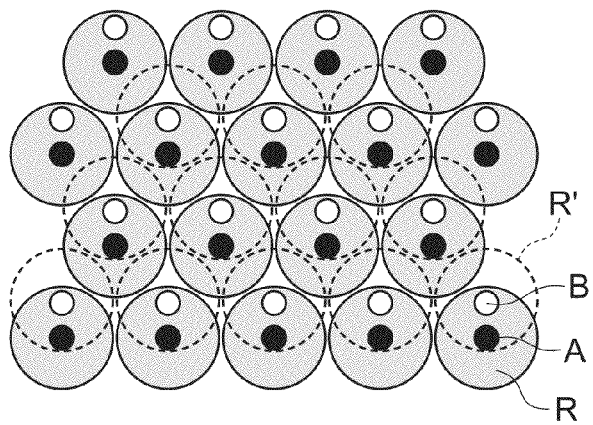
FIG. 22 shows a case where a plurality of receptive fields are spatially overlaid one on the other as another example of arrangement of electrodes with respect to the plurality of receptive fields.

As shown in FIG. 22, the receptive areas R and receptive areas R', which are drawn by a solid line and a dashed line, respectively, are overlaid one on the other. Also in such a case, the set of electrodes (A and B) is capable of inputting the above-mentioned predetermined electrical stimulation pattern signal in the receptive fields drawn by a solid line and a dashed line. It should be noted that in this example, if the receptive fields R and the receptive fields R' are compared, the center area Ra and the surrounding area Rb are replaced with each other with respect to the arrangement of the set of electrodes (A and B).

Figure 23A:
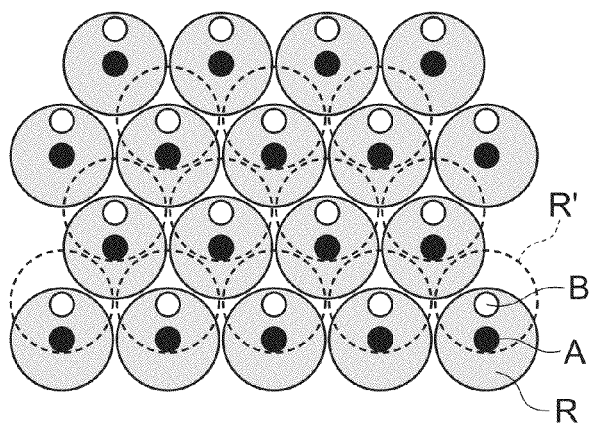
FIGS. 23A and 23B show an example in which input of the stimulation pattern signals by the sets of electrodes is switched.
Figure 23B:
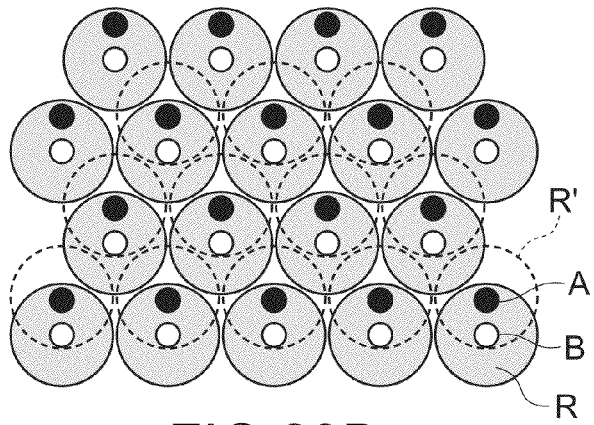

In FIG. 22, for example, in the case where the receptive fields R drawn by a solid line are on-center receptive fields, and the receptive fields R' drawn by a dashed line are off-center receptive field, the following driving method can be performed. For example, the above-mentioned stimulation pattern signals of the electrodes A and B can be replaced with each other to be used as shown in FIGS. 23A and 23B, in the case where a target receptive filed to which electrical stimulation is applied is an on-center receptive field and the case where the target receptive field is an off-center receptive field.

4. Stimulation Pattern Signal According to Other Embodiments

FIGS. 24 to 27 show other examples of the Benham's top. FIGS. 24, 25, 26, and 27 show examples in which subjective colors of red, orange, green, and blue are generated, respectively, and their stimulation patterns are represented by patterns P5 to P8. In this embodiment, 1 clock (reference clock) is ⅙ of the cycle T (e.g., in the case where the frequency is 7 Hz, 1 clock is 0.024 seconds), and the black area corresponds to T/3. The rotation direction is a counterclockwise direction, and a block arrow represents a position of time 0.

Examples of the electrical stimulation pattern signals input to the receptive fields, which correspond to the above-mentioned stimulation patterns P5 to P8, are shown in the following formulae 9 to 16.

$$\text{Electrode } A: I_{ar}(t) = \{0(0 \leq t < T/2), A(T/2 \leq t < T)\} \quad \text{Formula 9}$$

$$\text{Electrode } B: I_{br}'(t) = \{0(0 \leq t < T/3), A(T/3 \leq t < T)\} \quad \text{Formula 10}$$

$$\text{Electrode}/A: I_{ao}(t) = \{0(0 \leq t < T/3), 0(T/2 \leq t < 2T/3), A(T/3 \leq t < T/2), A(2T/3 \leq t < T)\} \quad \text{Formula 11}$$

$$\text{Electrode } B: I_{bo}'(t) = \{0(0 \leq t < T/3), A(T/3 \leq t < T)\} \quad \text{Formula 12}$$

$$\text{Electrode}/A: I_{ag}(t) = \{0(0 \leq t < T/3), 0(2T/3 \leq t < 5T/6), A(T/3 \leq t < 2T/3), A(5T/6 \leq t < T)\} \quad \text{Formula/13}$$

$$\text{Electrode } B: I_{bg}'(t) = \{0(0 \leq t < T/3), A(T/3 \leq t < T)\} \quad \text{Formula 14}$$

$$\text{Electrode } A: I_{ab}(t) = \{0(0 \leq t < T/3), 0(5T/6 \leq t < T), A(T/3t < 5T/6)\} \quad \text{Formula 15}$$

$$\text{Electrode } B: I_{bb}'(t) = \{0(0 \leq t < T/3), A(T/3 \leq t < T)\} \quad \text{Formula 16}$$

As described above, the clock cycle or the ratio of the black area to the entire Benham's top can be set as appropriate.

Figures 28, 29:
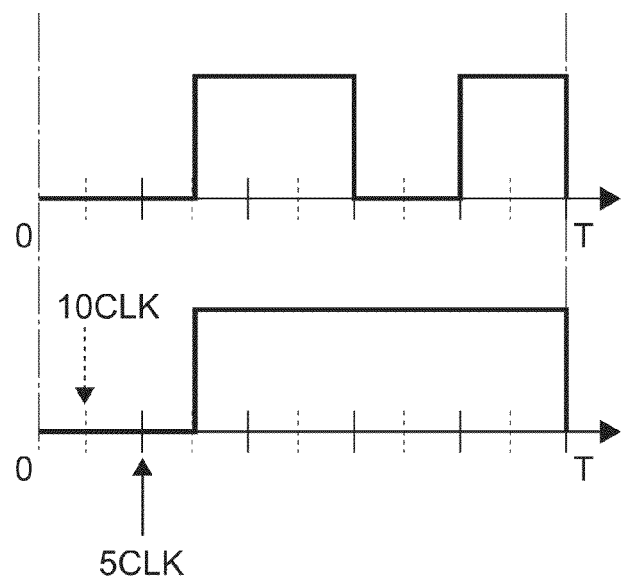
FIG. 28 is a table showing a relationship between each presentation color by the stimulation pattern and RGB.
FIG. 29 shows another example of a clock of the electrical stimulation pattern signal.

FIG. 28 is a table showing a relationship between each presentation color by the stimulation patterns P1 to P8 described above and RGB. For example, in the case where the signal generation unit 15 obtains information on color from the outside, the signal generation unit 15 can obtain RGB information as the information on color, refer to a table, generate the electrical stimulation pattern signal by the stimulation patterns P1 to P8 based on the obtained information on color, and input the generated electrical stimulation pattern signal to the receptive field. In the case where a group of patterns including the stimulation pattern P1 to P4 is referred to as a control mode 1 and a group of patterns including the stimulation pattern P5 to P8 is referred to as a control mode 2, the signal generation unit 15 may switch between the controls modes 1 and 2.

For example, in FIG. 6, 24, or the like, in the period of time when the point Pr and Pr' are in a dark state, i.e., in the period of time when stimulation at an L level is applied in the point Pr and Pr', it is considered that firing of the ganglion cell can be stopped. The period of time is referred to as resting phase.

Although the duration of the resting phase is determined by the geometric constraint of dividing a circle in the stimulation patters P1 to p8 exemplified above, the resting phase can be set to be further shorter. For example, 1 cycle is 6 clocks in the stimulation pattern 7 shown in FIG. 26B, time modulation of pulse waveform may be performed with 1 cycle being 5 or 10 clocks, as shown in FIG. 29.

5. Configuration Example of Logical Circuit of Signal Generation Unit

Figure 30:
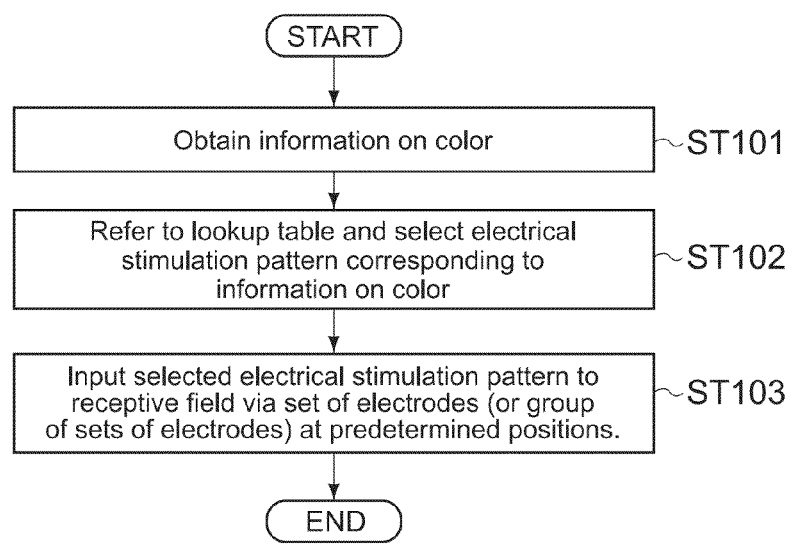
FIG. 30 is a flowchart showing a generation process of a pixel in an image performed by the signal generation unit.

FIG. 30 is a flowchart showing a generation process of a pixel in an image by the signal generation unit 15 (see FIGS. 3 and 4).

The signal generation unit 15 obtains information on color (Step 101). In this case, the signal generation unit 15 may obtain information on color from an external apparatus or obtain information on color stored in a memory in advance, as will be described later. The signal generation unit 15 converts the obtained information on color into an electrical stimulation pattern signal. Specifically, the signal generation unit 15 refers to a lookup table shown in FIG. 28, and selects an electrical stimulation pattern signal corresponding to the obtained information on color (Step 102). Then, the signal generation unit 15 inputs the selected electrical stimulation pattern to a receptive field via a set of electrodes (or a group of sets of electrodes) at a predetermined position (step 103).

Next, a process in which an image including a plurality of pixels is generated by the signal generation unit 15 will be described. Basically, the signal generation unit 15 is capable of generating at least 1 filed of image by performing the process in an amount of 1 pixel shown in FIG. 30 by the amount of a plurality of pixels.

Figure 31:
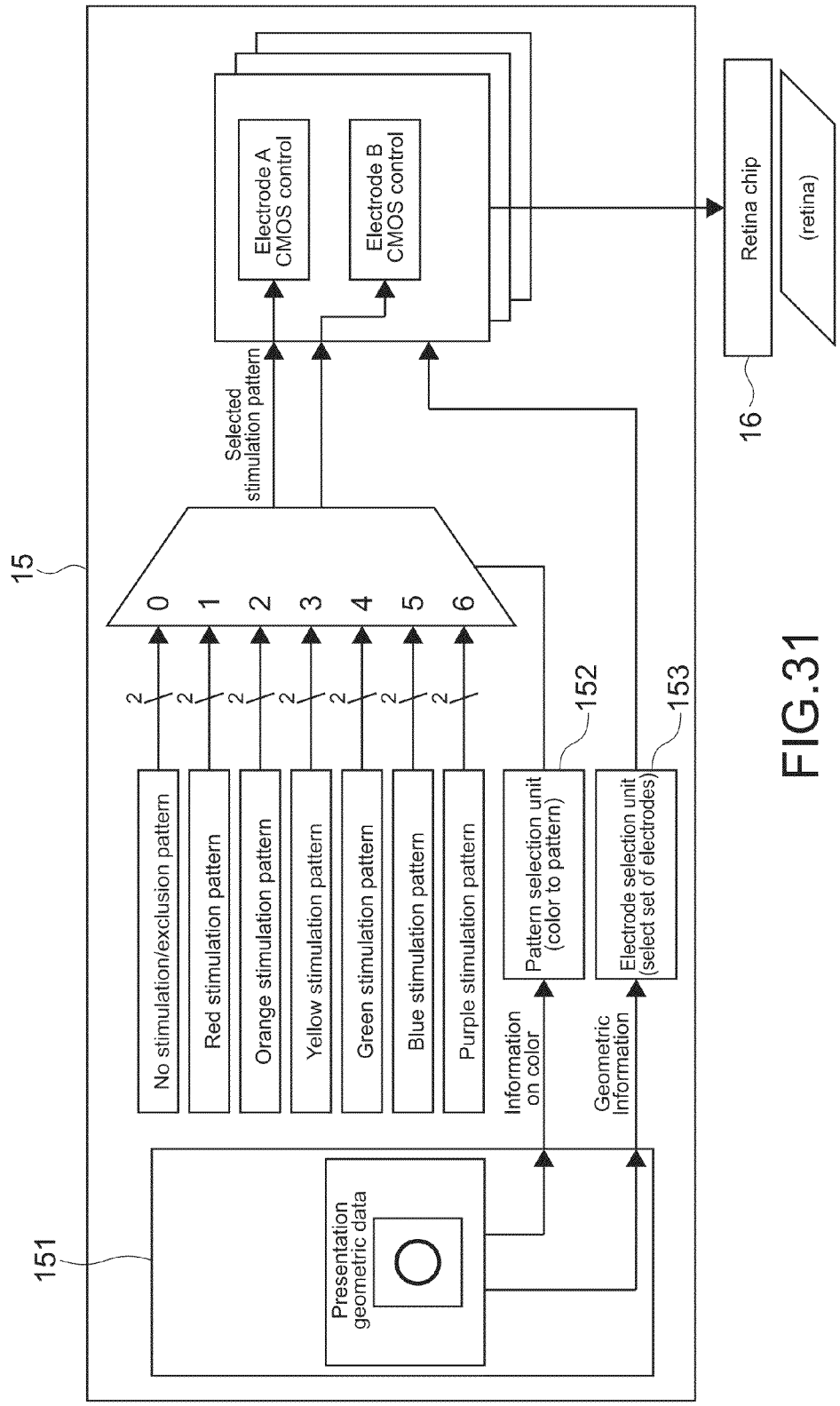
FIG. 31 is a block diagram showing a generation process of an image including a plurality of pixels performed by the signal generation unit.

FIG. 31 is a block diagram showing a configuration of the signal generation unit 15 of an image including a plurality of pixels. In this example, the signal generation unit 15 performs the process in an amount of 1 pixel shown in FIG. 30 by the amount of a plurality of pixels. Specifically, presentation geometric data including information on color and geometric information is generated by a presentation data generation unit 151. A pattern selection unit 152 selects a stimulation pattern corresponding to the information on color by referring to the lookup table shown in FIG. 28. Moreover, an electrode selection unit 153 selects a set of electrodes or a group of electrodes of the retina chip 16 based on the geometric information.

A CMOS (Complementary Metal-Oxide Semiconductor) control unit 154 including a CMOS logic circuit or the like controls the electrode array unit 161 of the retina chip 16 depending on the selected pattern, the selected set of electrodes, and the like.

Figure 32:
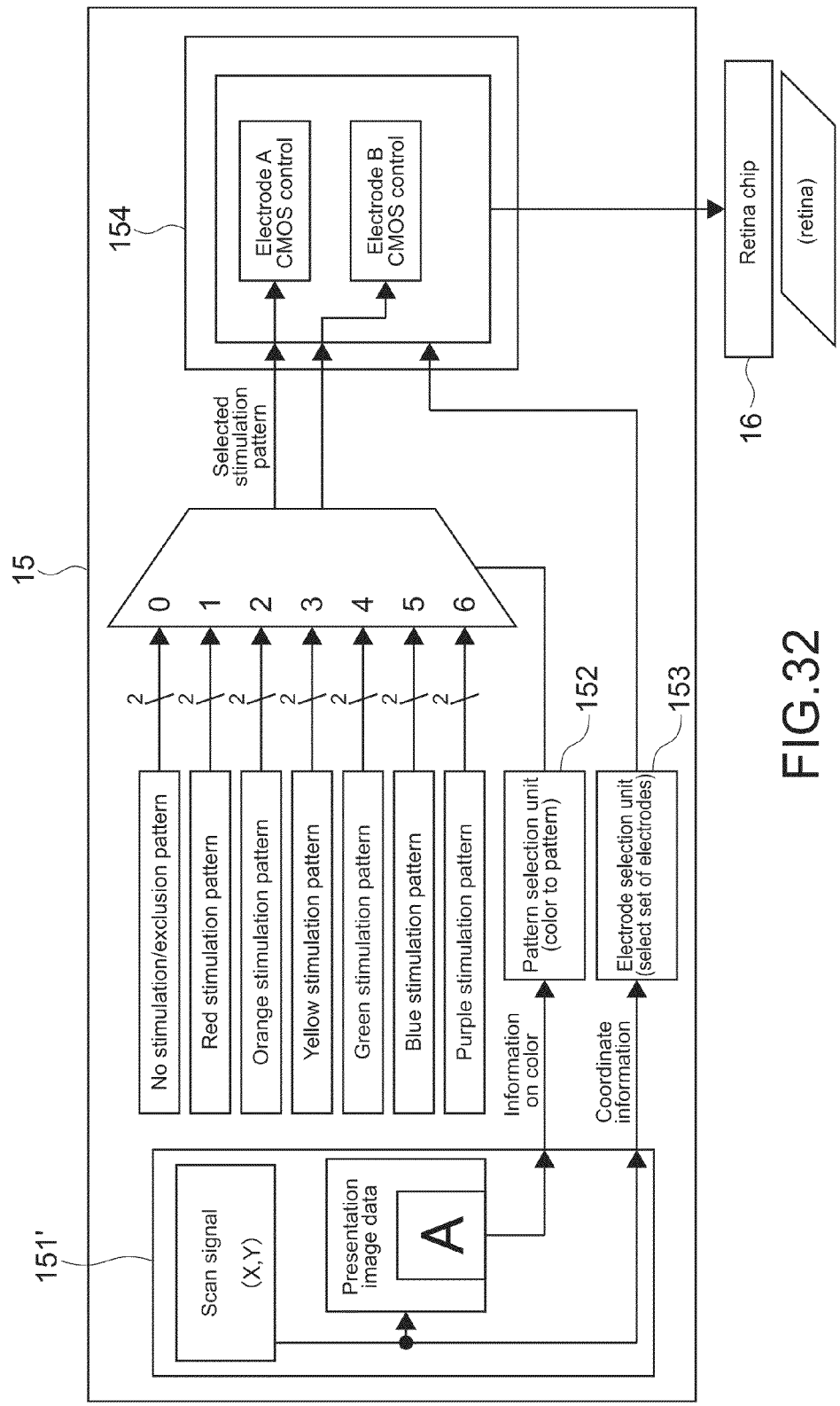
FIG. 32 is a block diagram showing a generation process of an image performed by a signal generation unit according to another example.

FIG. 32 is a block diagram showing a generation process of an image by the signal generation unit 15 according to another example. The signal generation unit 15 according to this example generates scan signals (X and Y) that scan the group of sets of electrodes of the retina chip 16, and transmits the scan signal to the electrode selection unit 153 as coordinate information.

6. Another Application Example of Present Disclosure

Figure 33:
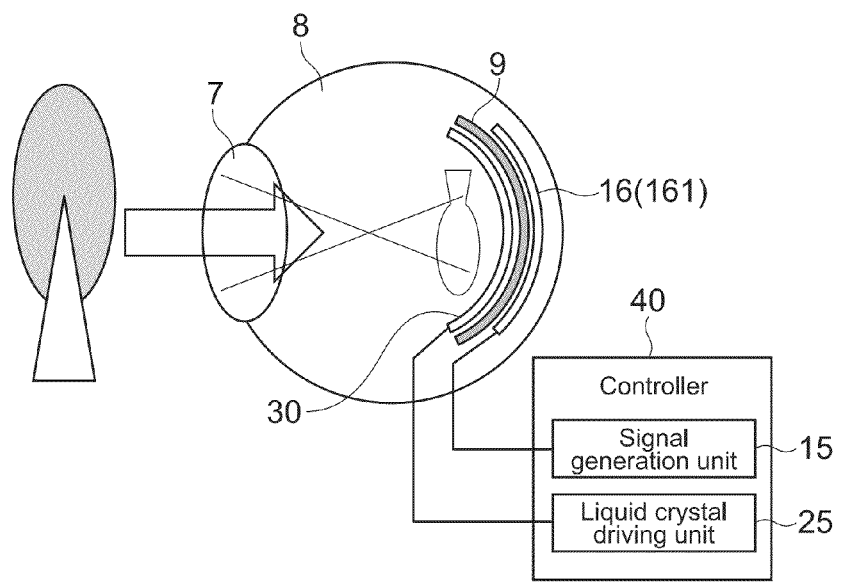
FIG. 33 shows an embodiment in which input of the vision from a pupil and input of stimulation by the signal generation unit are switched by using a liquid crystal cell.
Figure 34:
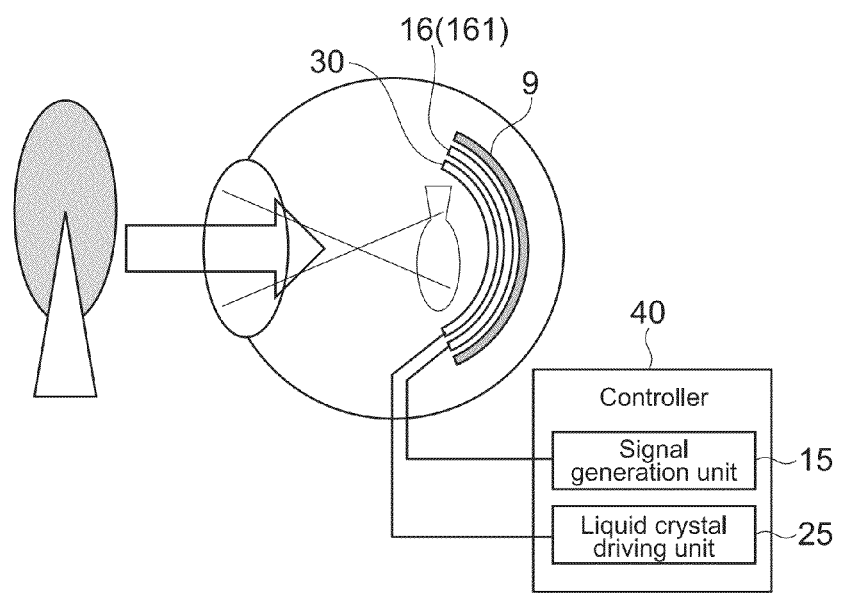
FIG. 34 shows another example of the embodiment shown in FIG. 33.

FIGS. 33 and 34 each show an embodiment in which a controller 40 switches between input of a field of view from a pupil and input of stimulation by the signal generation unit 15 by using a liquid crystal cell 30.

In the embodiment shown in FIG. 33, the liquid crystal cell 30 is arranged on the front side of the retina 9 and in a crystalline lens 7 or on the backward side of the crystalline lens 7, and the retina chip 16 (electrode array unit 161) is arranged on the backward side of the retina. The liquid crystal cell 30 is driven by a liquid crystal driving unit 25.

On the other hand, in the embodiment shown in FIG. 34, the liquid crystal cell 30 and the retina chip 16 are arranged on the front side of the retina 9 and backward side of the crystalline lens 7, and the liquid crystal cell 30 is arranged on the front side of the retina chip 16. In this case, the electrode of the retina chip 16 is a transparent electrode.

Figure 35:
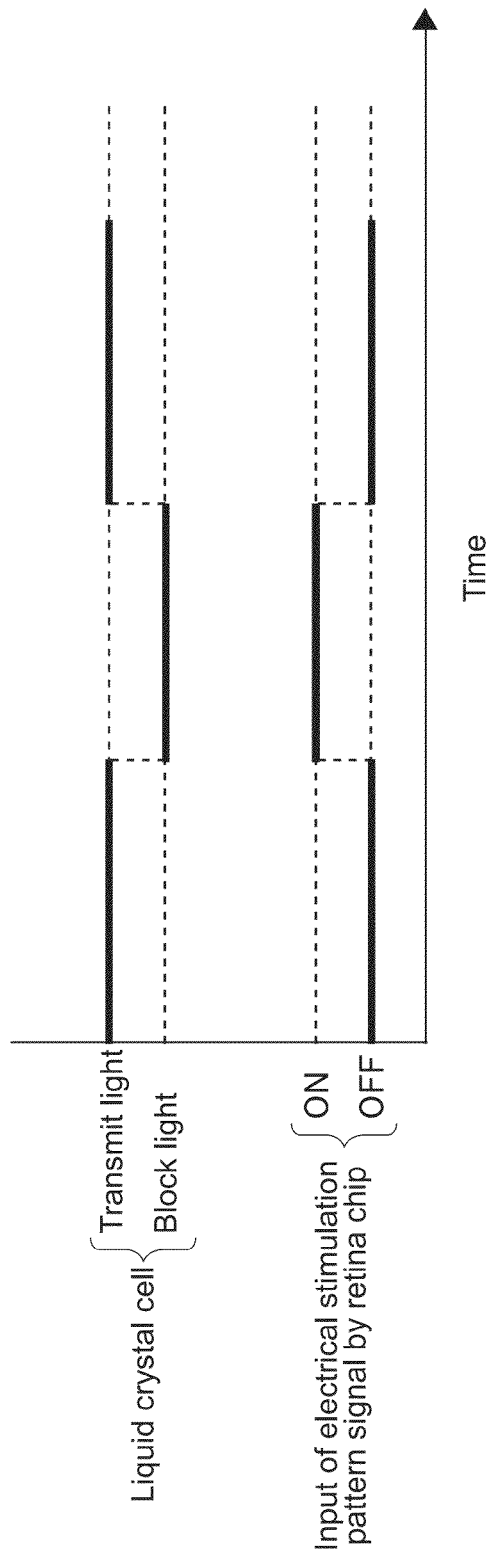
FIG. 35 shows a chart of driving timing of the liquid crystal cell and input timing of the electrical stimulation pattern signal by the retina chip in the embodiments shown in FIGS. 33 and 34.

FIG. 35 shows a chart of driving timing of the liquid crystal cell 30 and input timing of the electrical stimulation pattern signal by the retina chip 16 in the embodiments shown in FIGS. 33 and 34. The controller 40 causes natural light from the outside to be input to the retina 9 during the period of time when light is transmitted through the liquid crystal cell 30, and stops generation of the electrical stimulation pattern signal by the signal generation unit 15. On the other hand, the controller 40 generates the electrical stimulation pattern signal and input the signal to the retina during the period of time when light is blocked by the liquid crystal cell 30.

As described above, the controller 40 switches input of an image of natural light and input of an artificial image generated by the signal generation unit 15, which enables human beings to perceive both of the images.

Moreover, by, for example, inputting a projection image reduced or deformed by the signal generation unit 15 to the retina, it is possible to cause human beings to perceive an external area, which is broader than that obtained by projecting natural light from the pupil on the retina, as an image.

7. Technical Effect Obtained by Present Disclosure

As described above, only information on shading of an achromatic color can be presented in the past. According to the present disclosure, however, it is possible to cause visual impairments or the like to perceive a color, i.e., intensity. Moreover, as described above, it is also possible to cause visual impairments or the like to perceive information on a character having an arbitrary shape or a graphic. Therefore, visual impairments can discriminate between a warm color and a cool color, enjoy a colored video, or know important information on a dangerous area or the like. Therefore, it is possible to increase the amount of information of an image the visual impairments can obtain.

Because the clock can be reduced to be about 20 to 50 ms, it is possible to save electric power and to achieve the downsizing and driving for a long time.

Because there is no need to use a color filter on the device side, it is possible to produce a device so as to be light in weight at a low cost.

8. Other Embodiments

The present disclosure is not limited to the above-mentioned embodiments and other various embodiments can be achieved.

The present disclosure can be applied to optogenetics. For example, in this case, light spatially and temporally modulated is applied to at least a part of the area ranging from a retina to a visual nerve via a light-emission probe. Specifically, by generating a stimulation pattern signal obtained not by electrical stimulation but by optical stimulation and inputting the signal to at least a part of the area ranging from a retina to a visual nerve, it is possible to generate a subjective color.

The signal generation unit 15 may obtain image information including information on color from an external apparatus, and generate a stimulation pattern signal based on the image information. The external apparatus may be a camera held by a user using the visual apparatus, or an external apparatus connected to the signal generation unit via a network such as WAN and LAN. In the case where the external apparatus is a camera, the camera may take an image (including a still image and a movie) of the surrounding area of the user, and the signal generation unit 15 may obtain information on the image in real time to generate a stimulation pattern signal.

It is also possible to combine at least 2 features of the feature portions in the embodiments described above.

9. The present disclosure can also take the following configurations.

(1) A visual apparatus, including:
  at least one set of probes including a plurality of probes; and
  a signal generation unit configured
    to generate a stimulation pattern signal corresponding to information on color, and
    to input, to at least a part of an area ranging from a retina to a visual nerve, a plurality of pattern signals as the generated stimulation pattern signal via the plurality of probes in the at least one set of probes.

(2) The visual apparatus according to (1), in which
  the signal generation unit is configured to generate the stimulation pattern signal for each of different colors.

(3) The visual apparatus according to (1) or (2), in which
  the signal generation unit is configured
  to generate a pair of pattern signals as the plurality of pattern signals, and
  to output each of the pair of pattern signals from at least two proves in the at least one set of probes.

(4) The visual apparatus according to (3), in which
  the at least two probes are disposed so that one of the pair of pattern signals is input to a center portion of a receptive field of the retina and the other of the pair of pattern signals is input to a peripheral portion of the receptive field of the retina.

(5) The visual apparatus according to (4), in which
  the signal generation unit is configured to generate a first pattern signal and a second pattern signal as the pair of pattern signals, the first pattern signal including a pulse having a first duration, the first pattern signal having a predetermined repeated cycle, the second pattern signal including a pulse having a second duration, the second pattern signal having the same repeated cycle as that of the first pattern signal, the second duration being shorter than the first duration.

(6) The visual apparatus according to (5), in which
  the signal generation unit has, in a case where the repeated cycle is represented by T, a reference clock of T/10 to T/5 for generating the pulse.

(7) The visual apparatus according to (1), further including
  a probe array unit including a plurality of sets of probes as the at least one set of probes, the plurality of sets of probes of the probe array unit being provided corresponding to a plurality of receptive fields of the retina.

(8) The visual apparatus according to (7), in which
  the signal generation unit is configured
  to select a group of sets of probes disposed at arbitrary positions out of the plurality of sets of probes, and
  to input the stimulation pattern signal.

(9) The visual apparatus according to (8), in which
  the signal generation unit is configured to select a group of sets of probes forming an arbitrary two-dimensional shape as the group of sets of probes disposed at arbitrary positions.

(10) The visual apparatus according to (7), in which
  the signal generation unit is configured to generate a phase difference between the stimulation pattern signals output from the plurality of sets of probes.

(11) The visual apparatus according to (10), in which
  the signal generation unit is configured
  to select a group of sets of probes disposed at arbitrary positions out of the plurality of sets of probes, and
  to generate the phase difference between the stimulation pattern signals out of the selected group of sets of probes.

(12) The visual apparatus according to any one of (4) to (11), in which
the receptive field is an area in a circle having a diameter of not less than 1 μm and not more than 30 μm.

(13) The visual apparatus according to any one of (1) to (12), in which
the signal generation unit is configured to generate a signal having a repeated cycle of not less than 3.5 Hz and not more than 10 Hz as the stimulation pattern signal.

(14) The visual apparatus according to any one of (1) to (13), in which
the signal generation unit is configured to generate one of an electric signal and an optical signal as the stimulation pattern signal.

(15) A visual method, including:
generating a stimulation pattern signal corresponding to information on color, the stimulation pattern signal including a plurality of pattern signals; and
inputting, to at least a part of an area ranging from a retina to a visual nerve, the plurality of pattern signals via a plurality of probes included in at least one sets of probes.

It should be understood by those skilled in the art that various modifications, combinations, sub-combinations and alterations may occur depending on design requirements and other factors insofar as they are within the scope of the appended claims or the equivalents thereof.

What is claimed is:

1. A visual apparatus, comprising:
an electrode array unit, including probes arranged in sets; and
a signal generation unit, configured
to generate a stimulation pattern signal corresponding to received data on color, and
to input a plurality of pattern signals from the stimulation pattern signal, to at least a part of an area ranging from a retina to a visual nerve, through the plurality of probes in at least one of the sets of probes; and,
to adjust the sensitivity of the input by varying the distance between respective sets of the probes.

2. The visual apparatus according to claim 1, wherein
the signal generation unit is configured to generate the stimulation pattern signal for each of different colors.

3. The visual apparatus according to claim 1, wherein
the signal generation unit is configured
to generate a pair of pattern signals as the plurality of pattern signals, and
to output each of the pair of pattern signals from at least two probes in the at least one set of probes.

4. A visual apparatus, comprising:
an electrode array unit, including of probes arranged in sets;
a signal generation unit, configured to:
generate a stimulation pattern signal corresponding to received data on color;
input a plurality of pattern signals from the stimulation pattern signal, to at least a part of an area ranging from a retina to a visual nerve, through the probes in at least one of the sets of probes;
generate a pair of pattern signals as the plurality of pattern signals; and
output each of the pair of pattern signals from at least two probes in the at least one set of probes; and
wherein the at least two probes are disposed so that one of the pair of pattern signals is input to a center portion of a receptive field of the retina and the other of the pair of pattern signals is input to a peripheral portion of the receptive field of the retina.

5. The visual apparatus according to claim 4, wherein
the signal generation unit is configured to generate a first pattern signal and a second pattern signal as the pair of pattern signals, the first pattern signal including a pulse having a first duration, the first pattern signal having a predetermined repeated cycle, the second pattern signal including a pulse having a second duration, the second pattern signal having the same repeated cycle as that of the first pattern signal, the second duration being shorter than the first duration.

6. The visual apparatus according to claim 5, wherein
the signal generation unit has, in a case where the repeated cycle is represented by T, a reference clock of T/10 to T/5 for generating the pulse.

7. The visual apparatus according to claim 4, wherein
the receptive field is an area in a circle having a diameter of not less than 1 μm and not more than 30 μm.

8. The visual apparatus according to claim 1, further comprising
a probe array unit including a plurality of sets of probes as the at least one set of probes, the plurality of sets of probes of the probe array unit being provided corresponding to a plurality of receptive fields of the retina.

9. The visual apparatus according to claim 8, wherein
the signal generation unit is configured
to select a group of sets of probes disposed at arbitrary positions out of the plurality of sets of probes, and
to input the stimulation pattern signal.

10. The visual apparatus according to claim 9, wherein
the signal generation unit is configured to select a group of sets of probes forming an arbitrary two-dimensional shape as the group of sets of probes disposed at arbitrary positions.

11. The visual apparatus according to claim 1, wherein
the signal generation unit is configured to generate a signal having a repeated cycle of not less than 3.5 Hz and not more than 10 Hz as the stimulation pattern signal.

12. The visual apparatus according to claim 1, wherein
the signal generation unit is configured to generate one of an electric signal and an optical signal as the stimulation pattern signal.

13. A visual apparatus, comprising:
an electrode array unit, including of probes arranged in sets;
a signal generation unit, configured to:
generate a stimulation pattern signal corresponding to received data on color;
input a plurality of pattern signals from the stimulation pattern signal, to at least a part of an area ranging from a retina to a visual nerve, through the probes in at least one of the sets of probes; and
a probe array unit including a plurality of sets of probes as the at least one set of probes, the plurality of sets of probes of the probe array unit being provided corresponding to a plurality of receptive fields of the retina; and
wherein the signal generation unit is configured to generate a phase difference between the stimulation pattern signals output from the plurality of sets of probes.

14. The visual apparatus according to claim 13, wherein
the signal generation unit is configured
to select a group of sets of probes disposed at arbitrary positions out of the plurality of sets of probes, and
to generate the phase difference between the stimulation pattern signals out of the selected group of sets of probes.

15. A method comprising:
generating a stimulation pattern signal corresponding to received data on color, where the received stimulation pattern signal includes a plurality of pattern signals; and
inputting the plurality of pattern signals, to at least a part of an area ranging from a retina to a visual nerve, through a plurality of probes in at least one sets of probes; and
adjusting the sensitivity of the input by varying the distance between sets of probes.

* * * * *